United States Patent
Woerlee et al.

(10) Patent No.: US 8,481,304 B2
(45) Date of Patent: Jul. 9, 2013

(54) PHOTO BIOREACTOR WITH LIGHT DISTRIBUTOR AND METHOD FOR THE PRODUCTION OF A PHOTOSYNTHETIC CULTURE

(75) Inventors: Geert Feye Woerlee, Haarlem (NL); Ernst-Jan Siewers, Alkmaar (NL)

(73) Assignee: Feyecon B.V., Haarlem (NL)

( * ) Notice: Subject to any disclaimer, the term of this patent is extended or adjusted under 35 U.S.C. 154(b) by 324 days.

(21) Appl. No.: 12/933,654

(22) PCT Filed: Sep. 15, 2008

(86) PCT No.: PCT/NL2008/050604
§ 371 (c)(1),
(2), (4) Date: Dec. 13, 2010

(87) PCT Pub. No.: WO2009/116853
PCT Pub. Date: Sep. 24, 2009

(65) Prior Publication Data
US 2011/0117632 A1    May 19, 2011

(30) Foreign Application Priority Data

Mar. 19, 2008    (WO) ................ PCT/NL2008/050154

(51) Int. Cl.
*C12M 1/00*    (2006.01)
*G02B 26/08*    (2006.01)
*C12N 1/12*    (2006.01)

(52) U.S. Cl.
USPC ............ 435/292.1; 359/228; 435/257.1

(58) Field of Classification Search
USPC .............. 435/292.1, 257.1; 359/228
See application file for complete search history.

(56) References Cited

U.S. PATENT DOCUMENTS

| | | | |
|---|---|---|---|
| 5,162,051 A * | 11/1992 | Hoeksema | 47/1.4 |
| 6,287,852 B1 | 9/2001 | Kondo et al. | |
| 2005/0239197 A1* | 10/2005 | Katerkamp et al. | 435/292.1 |

FOREIGN PATENT DOCUMENTS

| | | |
|---|---|---|
| DE | 2406424 A1 | 8/1975 |
| JP | 08009809 A | 1/1996 |

OTHER PUBLICATIONS

Solar Bottle Bulbs (Age Defying Friends, http://agedefyingfriends.com/Solar_Bottle_Bulbs.html) 2002.*

* cited by examiner

*Primary Examiner* — Rosanne Kosson
(74) *Attorney, Agent, or Firm* — Browdy and Neimark, PLLC

(57) ABSTRACT

The invention provides a photo bioreactor comprising an aqueous liquid comprising a photosynthetic culture and a light distributor (30). Each light distributor has a surface arranged to receive light and a surface arranged to emit at least part of the received light. At least part of the surface is submerged in the aqueous liquid comprising the photosynthetic culture. The walls of the light distributors define a fluid filled cavity.

33 Claims, 12 Drawing Sheets

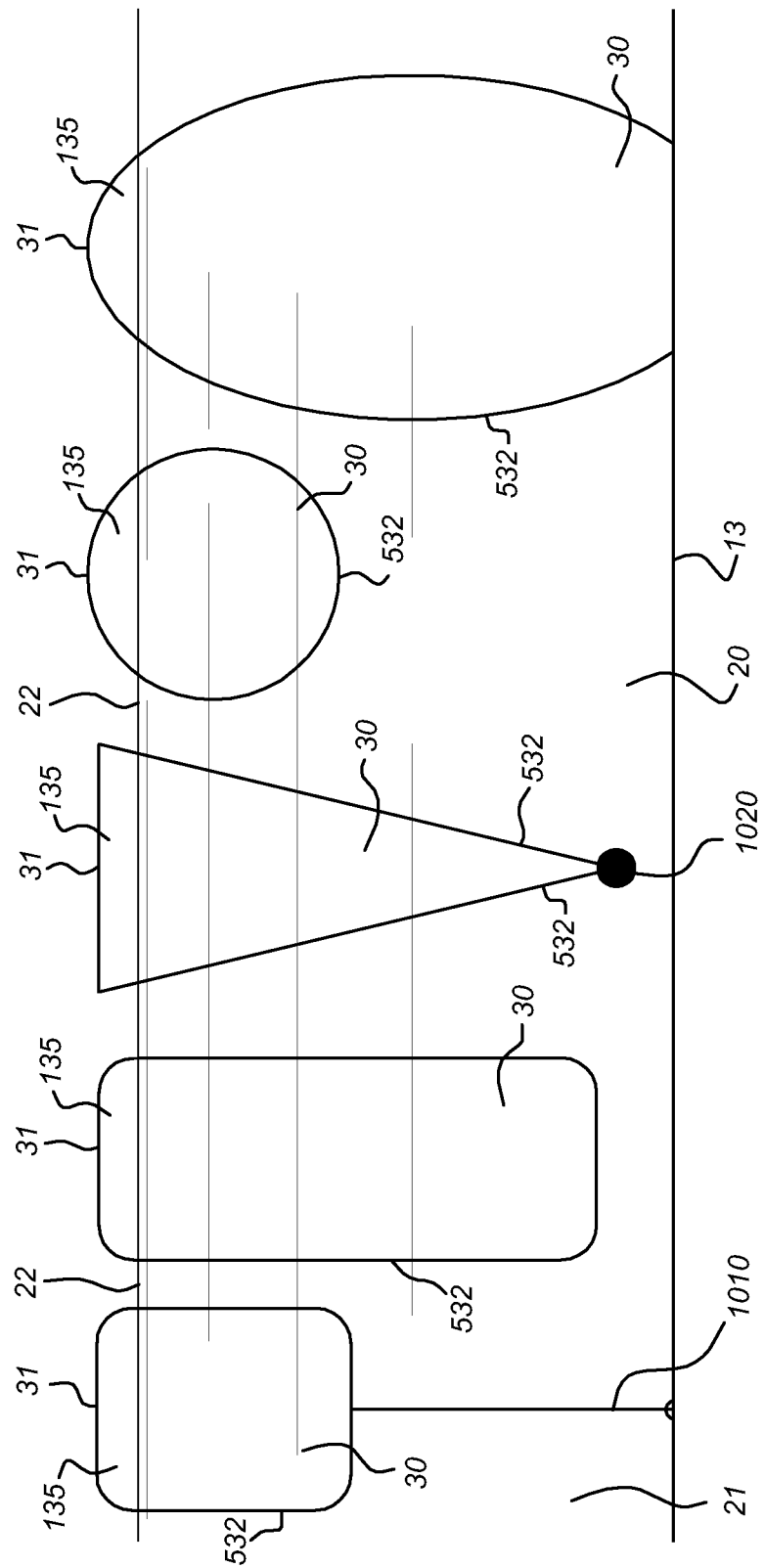

PHOTO BIOREACTOR WITH LIGHT DISTRIBUTOR AND METHOD FOR THE PRODUCTION OF A PHOTOSYNTHETIC CULTURE

FIELD OF THE INVENTION

The present invention relates to a photo bioreactor comprising an aqueous liquid comprising a photosynthetic culture and at least one light distributor. The invention further relates to such light distributor. The invention also relates to a method for the production of a photosynthetic culture in a bioreactor, as well as to the photosynthetic culture product obtainable by such method.

BACKGROUND OF THE INVENTION

Photo bioreactors for growing photosynthetic cultures such as algae are known in the art. It is a challenge to couple the light efficiently in the photosynthetic culture containing liquid. U.S. Pat. No. 3,986,297 for instance discloses a sealed double tank assembly for use in artificially cultivating photosynthetic substances such as chlorella. Accelerated growth of highly pure culture is obtained by means of a combination of a plurality of nozzles to emit mixed gases of carbon dioxide and ammonia, sources of light for intermittent application of light substantially similar to natural light, and agitator vanes for agitation of culture fluid in an inner tank, and an outer tank for temperature control. Here, the light source is not solar light, but is a xenon lamp, which is, according to U.S. Pat. No. 3,986,297, substantially similar to the natural light. U.S. Pat. No. 6,602,703 discloses a photo bioreactor for cultivating a photosynthetic organism. This photo bioreactor provides features that allow cleaning of the light source. The photo bioreactor has a container for containing a liquid culture medium for cultivating photosynthetic organisms and light-emitting tubes mounted within the container. The photo bioreactor also has cleaning devices mounted within the container for cleaning the outer surface of the light-emitting tubes and actuators for actuating the cleaning devices. The light tubes may be neon tubes. The above photo bioreactors apply artificial lighting. U.S. Pat. No. 4,699,086 uses solar light and discloses a fish feeding plant utilizing a solar ray collecting device and a algae cultivating device installed in the sea, a lake, or a pond, etc. The plant comprises a structure made of cylinders and constructed by vertically setting up cylinders in water and connecting the respective cylinders with each other by use of horizontal cylinders, a solar ray collecting device installed on the water surface above the structure, and a culture device for cultivating algae or the like installed in water. Solar rays are collected by the solar ray collecting device and are being transmitted to the culture device for cultivating the algae or the like through an optical conductor cable and employed as a photo-synthesis light source for the algae or the like. The culture device cultivates the algae by utilizing carbon dioxide $CO_2$, phosphorus, nitrogen, nutritious salt, etc. contained in water.

WO 05068605 describes a reactor for cultivating phototrophic micro organisms, wherein the sunlight is introduced in compartment walls by using one or more moveable collimators. The compartment walls are transparent and from there, light is distributed into the reactor. Such a reactor has an improved collection of radiation and an improved distribution of the radiation into the reactor, thereby providing a more efficient reactor and a more efficient cultivation of phototrophic micro organisms.

Further, Terry et al. in Enzyme Microb. Technol., 1985 (7), 474-487, Tredici et al. in Biotech. and Bioeng. 1998 (57), 187-197 and Mayer et al. in Biotech. and Bioeng. 1964 (VI), 173-190 describe designs for photo bioreactors.

SUMMARY OF THE INVENTION

A disadvantage of some of the prior are photo bioreactors described above is the application of artificial light, whereas preferably solar light is used, for instance because of energy and efficiency reasons. Further, an other disadvantage of some of the prior art photo bioreactors may be the sometimes inefficient incoupling of the solar light. In addition, some of the prior art photo bioreactors described above have a relatively complicated construction and use sometimes complicated optics to illuminate the liquid with photosynthetic culture.

Hence, it is an object of the invention to provide an alternative photo bioreactor, which preferably obviates one or more of the above mentioned disadvantages. It is further an object of the invention to provide a photo bioreactor with a relatively cheap construction and relatively cheap optics. Yet, it is further or alternatively an object to provide an alternative photo bioreactor which allows a good homogenization, such that the light distribution over the photo synthetic cultures is relatively even.

To this end, in a first aspect the invention provides a photo bioreactor comprising an aqueous liquid comprising a photosynthetic culture and at least one light distributor comprising at least one light receiving surface arranged to receive light and at least one emitting surface arranged to emit at least part of the received light, at least part of the emitting surface submerged in the aqueous liquid comprising the photosynthetic culture, and said light distributor comprising at least one fluid-filled sealed cavity comprising walls of elastomeric material, said fluid and elastomeric material in use being light transmitting from said light receiving surface to said light emitting surface.

An advantage of such photo bioreactor, and especially the use of the light distributor according to the invention is that it is possible to produce the light distributor in an extremely cheap manner. This allows vast areas like for instance areas of sea and lakes to be used in an economical way to produce large amounts of algae, for instance. To that end, the proposed light distributor assembly is extremely cheap to produce. Furthermore, it can be produced in mass production processes.

In an embodiment, the fluid has a pressure higher than the pressure of the environment, in particular above atmospheric pressure, for keeping said light distributor in its shape.

In an embodiment, the photo bioreactor a number of said light distributors, coupled to one another via a frame. Thus, an aligned set of light distributors with defined interspacing can be created.

In an embodiment, the light distributor or light distributors comprise an inlet and an outlet for said fluid.

In an embodiment with a number of light distributors, they are coupled to one another via said inlets and said outlets, and said inlets are coupled to said outlets in fluid connection or coupling for allowing the fluid to flow through various of said light distributors. Thus, forming of bio film can be prevented.

In an embodiment, the density of said fluid is lower than the density of the aqueous liquid. Usually, it is selected 5-20% lower. Selecting the density of the fluid with respect to the aqueous liquid makes it possible to set the position of the light distributors with respect to the surface of the aqueous liquid.

In an embodiment, the light receiving surface is thus above the surface of the aqueous liquid. The same effect may be achieved by designing the weight distribution of the light distributor. Another advantage of using a liquid with a lower density may be that the light distributors may be floating.

However, in another embodiment, the density of said fluid is higher than the density of the aqueous liquid. In such embodiment, light distributors may for instance be used that rest on the bottom of the reactor containing the aqueous liquid.

In an embodiment, the light distributor comprise a tip extending in said aqueous liquid comprising the photosynthetic culture, wherein said tip has a density which orients said light distributors tip-down in said aqueous liquid comprising the photosynthetic culture when said light distributors float in said aqueous liquid comprising the photosynthetic culture.

In an embodiment, the part of the light distributor which extends furthest in the aqueous liquid has a density above the density of the aqueous liquid.

In an embodiment, the part of the light distributor which extends furthest in the aqueous liquid has an alignment part. These above measures can provide proper orientation and positioning of the light distributors.

In an embodiment, the light distributor is formed from a sheet of plastic having holes forming at least part of said emitting surfaces extending in said aqueous liquid comprising the photosynthetic culture.

In an embodiment, the holes are vacuum formed indentations in said sheet of plastic.

In an embodiment, the light distributor is formed from a sheet of plastic having holes forming at least part of said emitting surfaces extending in said aqueous liquid comprising the photosynthetic culture and wherein said holes are indentations in said sheet of plastic which is formed via blow moulding or injection moulding. The indentations may also be formed in a film or sheet of plastic material using vacuum forming techniques which as such are well known to the skilled person. Subsequently, a further sheet or film or foil of plastic material may be sealed on the first sheet with indentations in order to seal the indentations. Prior, they can be filled with the fluid, or inlets and outlets for the fluid may be provided.

The invention further pertains to a photo bioreactor comprising an aqueous liquid comprising a photosynthetic culture and at least one light distributor comprising at least one light receiving surface arranged to receive light and at least one extending part extending in said aqueous liquid and having at least one emitting surface arranged to emit at least part of the received light, at least part of the emitting surface submerged in the aqueous liquid comprising the photosynthetic culture, said extending part of said light distributor comprising at least one fluid-filled sealed cavity comprising at least two plastic foil parts sealed together for forming said cavity.

The invention further pertains to a photo bioreactor comprising an aqueous liquid comprising a photosynthetic culture and at least one light distributor comprising at least one light receiving surface arranged to receive light and at least one extending part extending in said aqueous liquid and having at least one emitting surface arranged to emit at least part of the received light, at least part of the emitting surface submerged in the aqueous liquid comprising the photosynthetic culture. In this embodiment, said extending part of said light distributor comprising at least one fluid-filled sealed cavity and said light distributor is formed from at least one sheet of plastic having holes forming said cavities forming at least part of said emitting surfaces extending in said aqueous liquid comprising the photosynthetic culture.

The invention further pertains to a photo bioreactor comprising an aqueous liquid comprising a photosynthetic culture and at least one light distributor comprising at least one light receiving surface arranged to receive light and at least one extending part extending in said aqueous liquid and having at least one emitting surface arranged to emit at least part of the received light, at least part of the emitting surface submerged in the aqueous liquid comprising the photosynthetic culture. In this embodiment, said light distributor comprises a partially in said aqueous liquid comprising the photosynthetic culture submerged, fluid filled, light transmitting buoyant body.

Such a body receives light on a light receiving surface which in use usually extends a little above the surface of the aqueous liquid. This light is subsequently emitted by the emitting surface (or surfaces) which is/are submerged in the aqueous liquid. Thus, the body transmits the light from its receiving surface to its emitting surface. Thus, effectively the volume of the aqueous liquid in which the photosynthetic culture grown is enlarged, or the dose of light in the aqueous liquid is increased, or both.

In these further inventions, the features described in this description can be combined. These further inventions provide at least part of the advantages mentioned above.

In an embodiment, the photo bioreactor containing (during use) an aqueous liquid comprising a photosynthetic culture and a light distributor, especially a plurality of light distributors, wherein the (each) light distributor has a surface arranged to receive light and a tapered surface arranged to emit at least part of the received light, wherein at least part of the tapered surface is submerged in the aqueous liquid comprising the photosynthetic culture. The advantage of such photo bioreactor, and especially the use of the light distributor according to the invention, is that light may be distributed efficiently, such as to levels up to about 200-300 $\mu w/m^2$ in the aqueous liquid comprising the photosynthetic culture by relatively simple and cheap means. This concept allows a high illuminated volume fraction (ratio of the volume of the aqueous liquid comprising the photosynthetic culture that receives sufficient light for cell growth to the total volume of the aqueous liquid comprising the photosynthetic culture), for instance at least about 50%, more preferably at least about 80%. Whereas for instance in "normal" ponds during algae cultivation only an upper layer of the water can be used, with the invention light may penetrates deeper in the pond, and thus more photosynthetic culture is illuminated with light. Moreover, an optimal number of photons (about 50-400 $\mu mol/m^2/s$; depending on the culture) can be distributed throughout the cultures, whereas in state of the art ponds the upper layer receives a light level of light, which only partially can be used for the photosynthesis. Further, with the photo bioreactor according to embodiments of the invention relative large areas of photosynthetic cultures may be cultivated.

The light distribution can even be enhanced by adding reflectors to the tapered surface. Hence in an embodiment, at least part of the tapered surface comprises a reflector arranged to reflect at least part of the received light back into the light distributor. Light may in this way be provided to the aqueous liquid even deeper below the liquid's surface.

In an embodiment, the light distributor has a shape selected from the group consisting of a conical shape, a parabolic shape and a pyramid like shape.

In yet another embodiment, the light distributor has a substantial spherical shape, such as for instance a balloon. The spherical shape may also be an elongated spherical shape.

In another embodiment, the light distributor is a hollow body, wherein the hollow body is optionally suitable for containing a liquid, for instance water. When the hollow light distributor is filled with water (and/or another liquid), the number of reflections within the light distributor may increase. In this way, light may also be provided to the aqueous liquid even deeper below the liquid's surface. As will be clear to the person skilled in the art, the liquid contained by the light distributor in embodiments wherein the light distributor is a hollow body (filled with such liquid), such liquid is preferably transparent for light. Suitable liquids may for instance be selected from one or more (i.e. a mixture) of the group consisting of water, ethanol, glycerol, and γ-butyrolactone, especially from the group consisting of water, ethanol and glycerol. Further, such hollow light distributors are preferably liquid tight, i.e. the liquid contained by the light distributor and the aqueous liquid from the photo bioreactor are separated from each other and can in principle not have contact; i.e. preferably the light distributor is hermetically sealed. The light distributor may also comprise a plurality of materials. For instance, in an embodiment, the hollow light distributor is filled with another solid transparent material. Hence, the cavity of the hollow body may at least partially be filled with (i.e. comprise) a liquid and/or may be at least partially be filled with (i.e. comprise) a solid.

In an embodiment, the photo bioreactor further comprises a second body, the second body comprising a cavity having a tapered surface, wherein the light distributor and the second body are arranged in a configuration wherein the light distributor is at least partly arranged in the cavity and wherein there is a distance between the tapered surface of the cavity of the second body and the tapered surface of the light distributor. Preferably, the cavity and the light distributor have substantially corresponding shapes. In this way, the second body and the light distributor(s) can be arranged in a male-female arrangement and a substantially homogeneous flow between the tapered surface(s) of the cavity(cavities) and the tapered surface(s) of the distributor(s) can be obtained. Preferably, at least part of the void(s) between the tapered surface(s) of the cavity(cavities) and the tapered surface(s) of the distributor(s) has a constant width, i.e. that at least part of the tapered surface(s) of the cavity(cavities) and at least part of the tapered surface(s) of the distributor(s) are arranged at a constant distance.

Hence, in certain embodiments, the photo bioreactor according to the invention comprises a plurality of light distributors and optionally further comprises a second body comprising a plurality of cavities.

In an embodiment, the photo bioreactor further comprises a construction, wherein the construction comprises the plurality of light distributors. The light distributors may for instance be arranged in such construction or be integrated in the construction. In a specific embodiment, the construction comprising the plurality of light distributors is a corrugated construction, and the light distributors are corrugations. The light distributors may for instance have tapered surfaces which are wedge-shaped (or V-shaped) or curved, i.e. the corrugations may be wedge-shaped (or V-shaped) or curved, especially parabolically curved. During use of the photo bioreactor, the corrugations are arranged with at least part of the tapered surface submerged in the aqueous liquid comprising the photosynthetic culture. As will be clear to the person skilled in the art, the construction may also comprise a combination of wedge-shaped (or V-shaped) and curved distributors (i.e. here especially corrugations).

Therefore, in an embodiment, the invention provides a photo bioreactor comprising (during use) an aqueous liquid comprising a photosynthetic culture and a plurality of light distributors, wherein the light distributors have surfaces arranged to receive light and tapered surfaces arranged to emit at least part of the received light, wherein at least part of the tapered surfaces are submerged in the aqueous liquid comprising the photosynthetic culture, wherein the photo bioreactor further comprises a construction comprising the plurality of the light distributors, wherein the construction comprising the plurality of light distributors is a corrugated construction, and wherein the light distributors are corrugations.

In an embodiment, the photo bioreactor further comprises a second body, the second body comprising a plurality of cavities having tapered surfaces, wherein the light distributors and the second body are arranged in a configuration wherein the light distributors is at least partly arranged in the cavities and wherein there is a distance $d2$ between the tapered surfaces of the cavities of the second body and the tapered surfaces of the light distributors, wherein the plurality of cavities form a corrugated counter construction, and wherein preferably the cavities and the light distributors have substantially corresponding shapes (male-female arrangement).

In an embodiment, the construction and the second body are one reactor body. Even more especially, the construction and the second body are an extruded reactor body. In this way, the reactor may be easily produced, handled and transported. A further advantage is that mass production is relatively easily possible, which allows use of large areas of the reactors. In a specific embodiment, a plurality of reactors is applied, wherein channels of adjacent reactors are connected to each other.

In an embodiment, the construction and the second body (especially the corrugated counter construction) are arrange to provide substantially parallel channels for containing the aqueous liquid comprising the photosynthetic culture, wherein for instance the channels have a substantially wedge-shaped shape or a curved shape. Other shapes are however also possible, see also below.

In a further embodiment, the photo bioreactor is arranged to allow a flow of the aqueous liquid comprising a photosynthetic culture in a direction substantially parallel to the channels.

Therefore, according to a further aspect, the invention is also directed to such construction comprising a plurality of light distributors. Especially, the invention is also directed to a construction comprising a plurality of light distributors, wherein the construction is a corrugated construction, and wherein the light distributors are corrugations (i.e. are arranged to form a corrugated structure).

Further, the invention is in an aspect also directed to a reactor body comprising a corrugated construction and a corrugated counter construction, wherein the corrugated construction and the corrugated counter construction are arranged to provide substantially parallel channels between the corrugated construction and the corrugated counter construction for containing an aqueous liquid comprising a photosynthetic culture.

Even more especially, the corrugations of the corrugated construction and the corrugations of the corrugated counter construction may independently have shapes which are selected from the group consisting of parabolic shapes, sine like shapes, wedge-shape shapes (V-shaped shapes) and block-wave shapes, especially selected from the group consisting of parabolic shapes, sine like shapes, and wedge-shape shapes. This means that the corrugations of the corrugated construction have shapes which are selected from the group consisting of parabolic shapes, sine like shapes, wedge-shape shapes and block-wave shapes and the corrugations of the corrugated counter construction have independently shapes which are selected from the group consisting of parabolic shapes, sine like shapes, wedge-shape shapes and block-wave shapes. Other shapes are however also possible. Therefore, the light distributors may also have shapes for instance selected from the group consisting of parabolic shapes, sine like shapes, wedge-shape shapes and block-wave shapes, especially from the group consisting of parabolic shapes, sine like shapes, and wedge-shape shapes.

The invention provides in a further aspect a method for the production of a photosynthetic culture comprising: providing an aqueous liquid and the photosynthetic culture, providing a light distributor according to the invention, especially a plurality of light distributors, or the construction according to the invention, and submerging at least part of the tapered surface(s) of the light distributor(s) in the aqueous liquid comprising the photosynthetic culture, and providing light to the surface(s) arranged to receive light of the light distributor(s). In further aspects, the invention provides the use of the light distributor or the construction according to the invention for distributing light in a photo bioreactor, and the use of the photo bioreactor according to the invention for the production of a photosynthetic culture (i.e. the formation of biomass).

According to a further aspect, the invention provides a photosynthetic culture produced by the method according the invention, especially wherein the photosynthetic culture comprises algae, even more especially wherein the photosynthetic culture comprises micro algae. Hence, a photosynthetic culture obtainable by the method of the invention is also part of the invention.

It should be clear that the aspects mentioned above can be combined to provide further advantageous effects. For instance, the specific shapes like wedge shape, curved for instance parabolic, or pyramid shapes can be used for the buoyant fluid filled bodies.

BRIEF DESCRIPTION OF THE DRAWINGS

Embodiments of the invention will now be described, by way of example only, with reference to the accompanying schematic drawings in which corresponding reference symbols indicate corresponding parts:

FIG. 5b is a side view of the elongated light distributor of FIG. 5a or 5b; FIGS. 5a and 5c are perspective views;

FIG. 11b shows a cross section through the light distributor assembly of FIG. 11a;

FIG. 14 shows several light distributor shapes and embodiments.

DETAILED DESCRIPTION OF THE PREFERRED EMBODIMENTS

Figure 1:
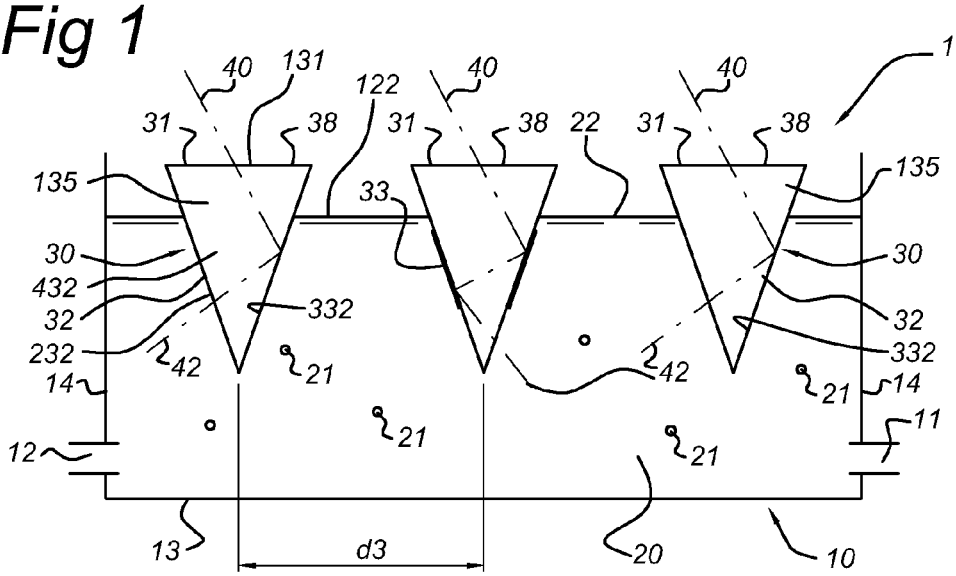
FIG. 1 schematically depicts in side view a general embodiment and variations thereon of the photo bioreactor and light distributors according to the invention.

FIG. 1 schematically depicts in side view a general embodiment and variations thereon of a photo bioreactor 1 and light distributors 30. The photo bioreactor 1 may comprises a reactor or vessel 10. Preferably, the photo bioreactor 1 of the invention is a closed photo bioreactor. However, the photo bioreactor 1 may also be open.

Vessel 10 may in an embodiment be a pond or a part thereof, a lake or a part thereof, a part of a brook, a part of a river, part of a canal, or a part of a sea. For instance, vessel 10 may be a man-made vessel with reactor bottom 13 and walls 14, but vessel 10 may also be a pond, or a part thereof, wherein walls 14 are arranged in the pond on the pond bottom 13 to obtain a vessel 10 in the pond. The invention will further refer to vessel 10. Herein, the "term man-made vessel" refers to vessels, containers or reactors wherein wall(s) 14 and bottom 13 are man made, such as a vessel comprising wall(s) 14 and bottom 13 of one or more materials selected from the group consisting of steel, plastic, concrete and other materials that can be used to assemble the vessel. In an embodiment, wall(s) 14 comprise a transparent material. The vessel 10 is arranged and constructed to contain liquid 20. In embodiments described below, the vessel 10 may also be absent. Hence, the photo bioreactor 1 may be comprise a vessel 10, but may in another embodiment also comprise internal channels (or "reactor channels").

The vessel 10 contains, at least during use of the photo bioreactor 1, an aqueous liquid 20, preferably water, comprising a photosynthetic culture 21. Hence, vessel 10 is arranged or constructed to contain during use the aqueous liquid 20 comprising a photosynthetic culture 21.

The photosynthetic culture 21 may comprise (micro) algae, but also other species that can convert radiation of the sun into biomass like for example photosynthetic purper bacteria. The living species that can be grown in a liquid and thereby form biomass and/or other useful material, and for which light is essential to grown, are herein indicated as photosynthetic cultures. With photosynthetic culture 21 are not only meant (green) algae, but all photosynthetic micro organisms, such as the cyanobacteria, the *Rhodophyta* (red algae), the *Chlorophyta* (green algae), *Dinophyta*, *Chrysophyta* (golden-brown algae), *Prymnesiophyta* (haptophyta), *Bacillariophyta* (diatoms), *Xanthophyta*, *Eustigmatophya*, *Rhaphidophyta*, *Phaeophyta* (brown algae) and photosynthetic purper bacteria. Suitable algae are known to the person skilled in the art. For example, *Dunaliella salina, Haematococcus pluvialis, Nannochloropsis* sp., *Chlorella* sp., *Chlamydomonas rheinhardtii, Arthrospira* sp., *Nostoc* sp, *Scenedesmus, Porphyridium, Tetraselmis, Spirulina* sp., etc. can be used. The photosynthetic culture 21 for use in this invention may comprise cell cultures of other organisms like genetically modified (micro) algae, genetically improved (micro) algae, etc. Also combinations of two or more different photosynthetic cultures may be applied as photosynthetic culture 21.

Advantageously, the invention provides vessel 10 wherein the liquid 20 comprises about 1-50 gram/l photosynthetic culture 21. Concentrations of about 5 up to 50 gram/l, or possibly even higher, may be obtained, whereas reactors for the cultivation of photosynthetic culture 21 of the state of the art may comprise liquids containing 2-3 gram/l photosynthetic culture 21. In this way, the reactor volume may be better utilised than it is the case for reactors in the state of the art.

The photo bioreactor 1 further comprises light distributor 30. Herein the term "a light distributor" also includes a number of light distributors. The light distributor 30 has a surface 31 arranged to receive light 40 and a light emitting surface 532, here a tapered surface 32, arranged to emit at least part of the received light 40. Surface 31 may therefore also be indicated as light receiving surface 31 and surface 32 may therefore also be indicated as light emitting surface 532. During use of the photo bioreactor 1, the light distributor(s) 30 are arranged in reactor 1 with at least part of the surface 31 above the liquid's surface 22, but preferably the entire surface 31 is found above the liquid surface 22. Likewise, during use of the photo bioreactor 1, the light distributor(s) 30 are arranged in reactor 1 with at least part of the tapered surface 32 in the liquid 20. Preferably at least about 50%, such as about 50-80%, more preferably at least about 70%, such as about 70-90%, and more preferably at least approximately 90%, such as about 90-100%, of the tapered surface 32 is immersed in the liquid during operation of the photo bioreactor 1.

The light distributor 30 may optionally comprise a fluid. This fluid is herein indicated with reference 135. For the sake of understanding, most of the herein schematically depicted embodiments are shown with light distributors 30 containing such fluid 135, but the invention is not limited to such embodiments.

The light distributors 30 may in an embodiment be constructed to be floating. The person skilled in the art knows how to make objects floating, for instance by selecting the type of material and its specific gravity, the shape, the presence of air chambers, etc. The light distributor 30 has a top surface 38, which may comprise an opening. When top surface 38 is closed, the top surface 38 comprises the light receiving surface 31 (i.e. including the embodiment wherein the top surface 38 substantially consists of the light receiving surface 31), when the top surface 38 is open, light 40 may penetrate substantially unhindered to the edges of the light distributor. Such opening may especially be arranged to allow light 40, such as sun light, penetrate into a hollow light distributor 30 (see also below).

Figure 6A:
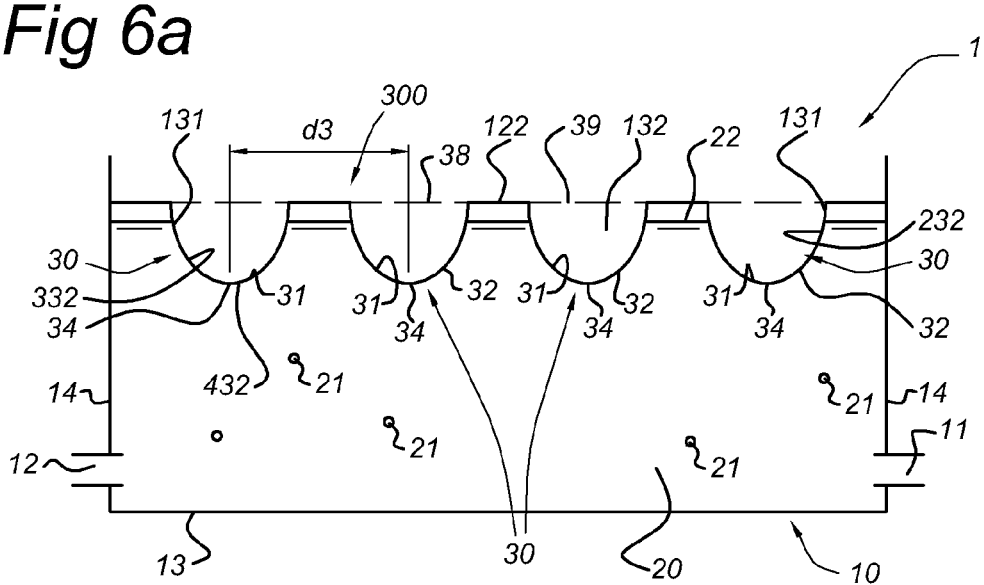
FIGS. 6a-6c schematically depict embodiments of constructions comprising light distributors, wherein FIG. 6a schematically depicts as side view of such construction in a photo bioreactor, FIG. 6b schematically depicts in perspective an embodiment of the construction (such as from FIG. 6a), and wherein FIG. 6c schematically depicts an alternative construction with a plurality of light distributors (which are not elongated), and wherein the light distributors have parabolically tapered surfaces.
Figure 6B:
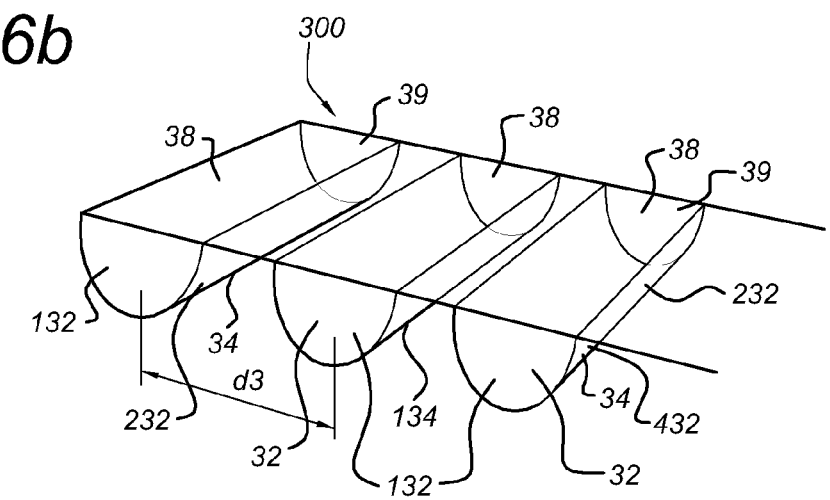
Figure 6C:
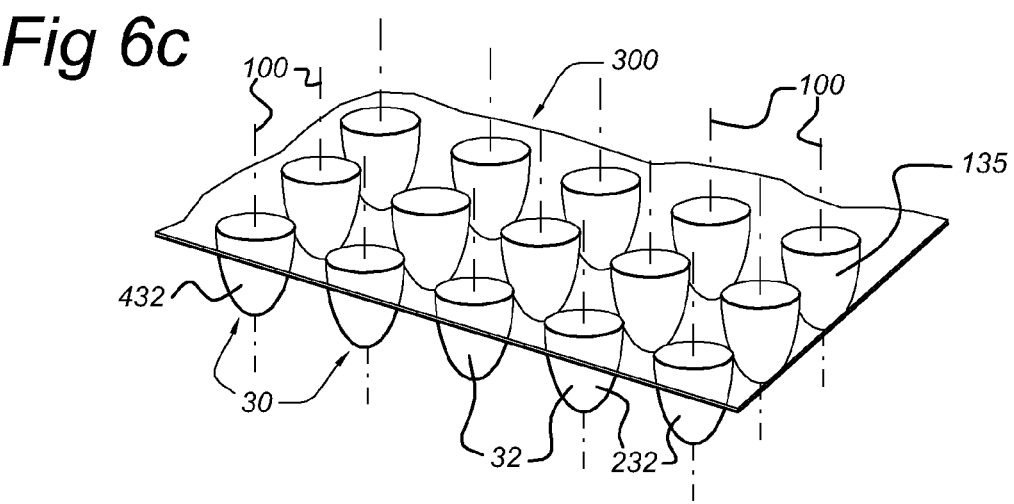

However, the light distributor(s) 30 may also be contained in a construction arranged over or in the liquid 20. Such construction is arranged to maintain at least part of the tapered surface 32 during use below the liquid's surface 22 and at least part of the surface 31 arranged to receive light 40 above the liquid's surface 22 (see also above). Embodiments of such construction are schematically depicted in FIGS. 6a-6c (see below).

Advantageously, the light distributor(s) 30 according to the invention may thus be used for distributing light in a photo bioreactor 1, which photo bioreactor 1 may in an embodiment be arranged in vessel 10, wherein the vessel 10 is for instance a pond or a part thereof, a lake or a part thereof, a part of a brook, a part of a river, part of a canal, or a part of a sea. By containing the liquid between walls 14 and bottom 13 and arranging the light distributors 30 in the liquid 20, photo bioreactor 1 is obtained, wherein algae, etc. can be cultivated. Part of the light distributors 30 will protrude from the liquid 20 (i.e. extend from the liquid 20), and this part can receive light 40. In this way, natural ponds, etc. can easily be used as photo bioreactors 1. Hence, the invention also provides a light distributor 30 per se having a surface 31 arranged to receive light 40 and tapered surface 32 arranged to emit at least part of the received light 40. The light distributor 30 according to the invention is especially a light distributor 30 for a photo bioreactor comprising a vessel containing aqueous liquid 20 comprising the photosynthetic culture 21, the light distributor 30 having surface 31 arranged to receive light 40 from a source, such as the sun and/or an artificial source such as one or more lamps and/or one or more LEDs, arranged outside the aqueous liquid 20 (i.e. above the liquid's surface 22 in the container or vessel 10), and tapered surface 32 arranged to emit at least part of the received light 40 into the aqueous liquid 20.

Hence, the light distributor(s) 30 are during use arranged such that at least part of the tapered surface 32 is submerged in the aqueous liquid 20 comprising the photosynthetic culture 21. The light distributor(s) 30 have a tapered part, having a tapered surface 32 and a part designed to receive light with a surface 31 arranged to receive light 40. During use, the surface 31 arranged to receive light is at least partially arranged above the liquid's surface 22. The photo bioreactor 1 may further comprise additional means to concentrate light 40 into the liquid 20. For instance, surface 31 of the light distributor(s) 30 may comprise lenses, etc.

As will be clear to the person skilled in the art, the material of the light distributor(s) 30 is essentially transparent. This means that at least part of the light distributor(s) 30, especially those parts that are necessary to receive light 40 and transport this light to at least part of the tapered surface 32 are transparent. Preferably, the light distributor(s) 30 is made of a transparent material. The term "transparent" is known to the person skilled in the art. Transparent herein especially indicates that visible light under perpendicular irradiation of a 1 cm thick piece of material is transmitted for at least about 70%, more preferably at least about 90%, even more preferably at least about 95%, up to substantially 100% transmission. Transparent materials which can be used may for instance be selected from the group consisting of glass, poly methyl acrylate (PMA), poly methyl methacrylate (PMMA) (Plexiglas or Perspex), cellulose acetate butyrate (CAB), polycarbonate (PC), poly vinyl chloride (PVC), polyethylene terephthalate (PET), and glycol modified polyethylene terephthalate (PETG). In another embodiment, the material comprises an acrylate, for instance PMA or PMMA, especially PMMA. Such materials are also known in the art as transparent plastics. In yet another embodiment, the material comprises transparent plastics commercially known as PERSPEX™ or PRISMEX™. Preferably, the light distributor 30 according to the invention essentially consists of a transparent material.

Due to the shape of the light distributor(s) 30, the received light will propagate to the light distributor(s) 30 and be transmitted and/or reflected at the tapered surface 32. Light that is transmitted can be absorbed by the photosynthetic culture 21 in the liquid 20 close to the tapered surface 32. Reflected light will propagate further through the light distributor(s) 30 and meet with another part of the tapered surface 32 and may there be transmitted and/or reflected. The more reflections, the lower the received light 40 penetrates into the light distributor(s) 30 (and thus the lower in the vessel 10 the received light 40 may be absorbed by the photosynthetic culture 21). Light transmitted into the liquid 20 is indicated with reference number 42.

The distance between the light distributors 30, indicated as distance d3 between the end parts or "tops" of the tapered surface 32, may be about 2-200 cm.

In order to promote the number of reflections, in an embodiment at least part of the tapered surface 32 comprises a reflector 33 arranged to reflect at least part of the received light 40 back into the light distributor 30. In FIG. 1, such reflector 33 is shown. Preferably, the reflector occupies in the range of about 10-90% of the tapered surface 32; preferably, reflectors are only arranged in/on the upper part of the tapered surface 32. Reflectors are known in the art, and may for instance comprise reflective foils. In an embodiment, the reflector 33 may also be arranged to transmit at least part of the received light 40 (for instance a reflector constructed to transmit between about 2-25% of the received light 40. The reflector(s) 33 may circumferentially surround at least part of tapered surface 32. The reflector 33 may circumferentially surround the light distributor 30, and may occupy in the range of about 10-90% of the tapered surface 32.

As mentioned above, the more reflections, the lower the received light 40 penetrates into the light distributor(s) 30 and thus the lower in the vessel 10 the received light 40 may be absorbed by the photosynthetic culture 21. Therefore, the light distributor(s) 30 preferably have a shape selected from the group consisting of a conical shape, a parabolic shape and a pyramid like shape. As will be clear to the person skilled in the art, the photo bioreactor 1 may comprise different types of light distributors 30 and during operation (during use) different types of light distributors 30 may be applied. Thus combinations of two or more different types of shapes of light distributors 30 may be applied in the photo bioreactor 1. In an embodiment parabolic shapes are preferred, since it appears that the incident light rays will remain trapped in higher proportion than for curved (round) shapes, and thus light may penetrated deeper in the liquid. Hence, the tapered surface 32 is especially "parabolically curved" or "parabolically tapered" or "parabolically curved tapered".

Figure 2A:
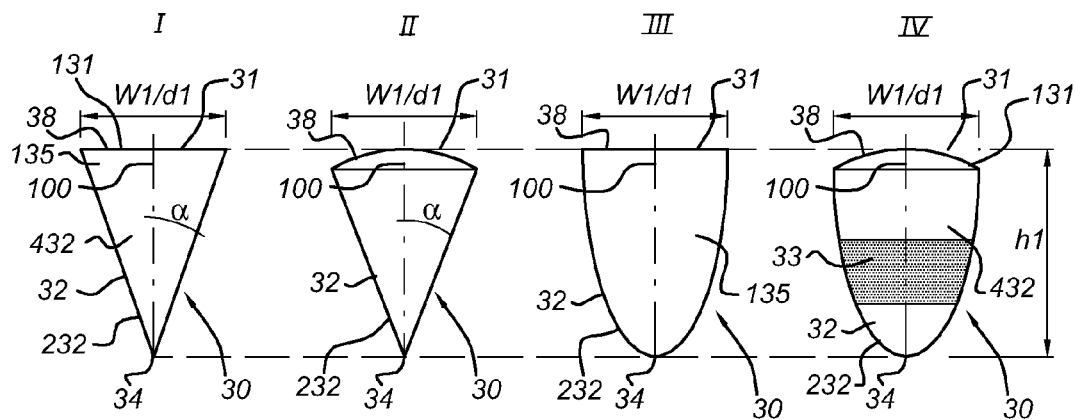
FIGS. 2a-2c schematically depict a number of light distributors seen from the side (2a,2c) and seen from the bottom (2b)
Figure 2B:
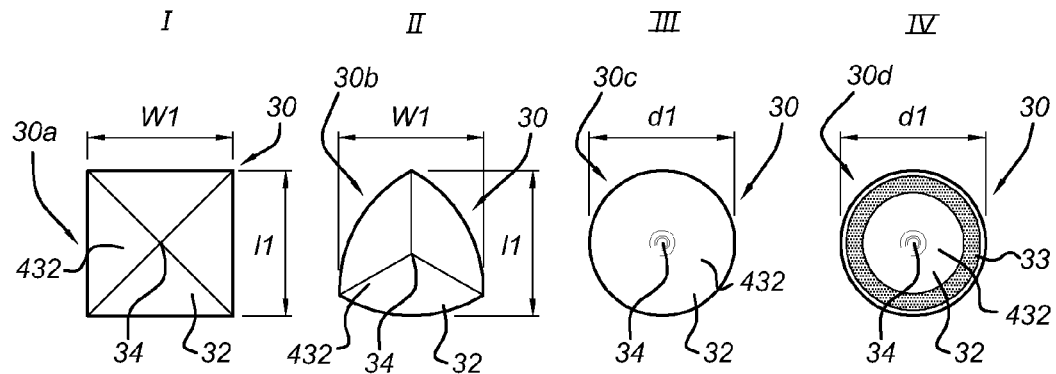
Figure 2C:
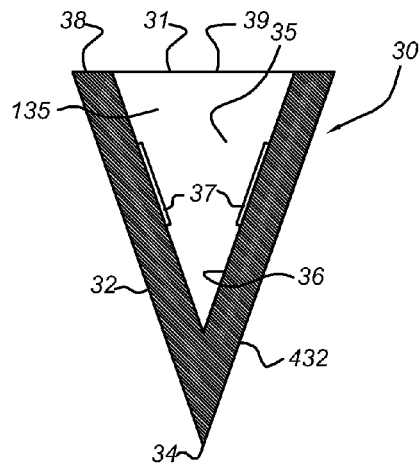

FIGS. 2a-2c schematically depict a non-limiting a number of possible types of light distributors 30. FIG. 2a schematically shows side views of possible light distributors 30 and FIG. 2b schematically shows views as seen from the bottom of the light distributors 30. The light distributors 30 have an apex or light receiving surface 31 and end part 34. End part 34 is in fact the top of the mathematical objects pyramid, tetrahedron or cone.

Herein, also truncated cones, tetrahedrons or pyramids may be used. Further, also other shapes may be used, such as pentagonal pyramids, triangular cupolas, square cupolas, pentagonal cupolas, pentagonal rotunda s, or elongated types thereof like elongated cones, elongated square pyramids, elongated tetrahedrons, elongated pentagonal pyramids, elongated triangular cupolas, elongated square cupolas, elongated pentagonal cupolas, elongated pentagonal rotundas. The light distributors may be regularly shaped, but may also be irregularly or asymmetrically be shaped. All these shapes, and other shapes are herein indicated as tapered shapes with tapered surfaces 32. As will be clear to the person skilled in the art, tapered surface 32 may thus also include a plurality of surfaces such as 3 (tetrahedron), 4 (square pyramid), etc. Herein, a surface 32 comprising a plurality of surfaces (see also schematic drawings of FIG. 2b), is indicated as surface 32. As will be clear to the person skilled in the art, the photo bioreactor 1 may comprise different types of light distributors 30 and during operation (during use) different types of light distributors 30 may be applied. Thus combinations of two or more different types of shapes of light distributors 30 may be applied in the photo bioreactor 1.

Herein, for the sake of simplicity further only cones, tetrahedrons and pyramids are discussed. These objects have a (optionally curved) base, which essentially comprises the light receiving surface 31 and a tapered part with a tapered surface 32, which tapers into an apex 34. Note that during use, the apex 34 will be in the liquid 20, whereas the base will at least partially, and more preferably entirely above the liquid's surface 22.

FIG. 2a, type I in shows a side view of a conical, tetrahedral or pyramidal light distributor 30; type II is the same as type I, however, the top surface 31, i.e. the surface arranged to receive light 40 is curved, here preferably convex. The tapered surface 32 forms an angle α with a longitudinal axis through the tapered body (i.e. the light distributor 30). Angle α is preferably in the range of about 1-45°, more preferably in the range of about 2-40°, even more preferably in the range of about 5-35°. Hence, in an embodiment, the tapered surface 32 is straight and has an angle α with a longitudinal axis 100 of the light distributor 30, preferably in the range of about 1-45°.

FIG. 2b shows on the left side views from the end part 34; i.e. seen along the longitudinal axis viewing from the apex 34 side. In case of a square pyramid, the first from left view will be found; in case of a tetrahedron, the second from left view will be found and in case of a cone one of the two right views will be found. By way of example, FIG. 2 shows from the left to the right a bottom view of a square pyramid with substantially flat surface 32 (although in an embodiment, the surface 32 may also be curved), a tetrahedron with curved surface 32 (although in an embodiment, the surface 32 may also be flat), a parabolic shape and again a parabolic shape, but now with reflector 33. Note that all schematically depicted light distributors 30 may comprise or may not comprise reflector 33 on or at least part of surface 32.

Hence, instead of (or in addition to) the light distributors 30 of types I and II, also light distributors 30 may be applied that have a curved tapered surface 32. These types are indicated in FIG. 2a as types III and IV. The person skilled in the art understands that substantially the same side views as seen from the end part 34 of types I and II will be found. Hence, in an embodiment the invention provides a light distributor 30 wherein the tapered surface 32 is curved. Types III and IV are herein also indicated as "parabolic shapes". Such types may have parabolically curved tapered surfaces 32.

For the sake of illustration, a conical type (which may be of types I-IV) with a reflector 33 is further indicated in FIG. 2b (right). In FIG. 2a such reflector 33 is by way of example only depicted in type IV, although all types may have such reflector 33. See also an example of a reflector comprising light distributor 30 in FIG. 1, wherein the middle light distributor 30 by way of example comprises a reflector 33.

The invention also provides a light distributor 30, wherein the light distributor 30 is a hollow body, and wherein the hollow body is optionally suitable for containing a liquid or a solid material. FIG. 2c schematically depicts such hollow type of light distributor 30. The light distributor 30 has a cavity 35 (light distributor cavity 35), with cavity wall(s) 36. Preferably, the cavity 35 is not filled with the photosynthetic culture 21 comprising aqueous liquid. Preferably, the cavity may be filled with water or another liquid; the cavity 35, optionally filled with a liquid or solid material, increases the number of reflections. The cavity may be closed, for instance by light receiving surface 31, or may be open, as schematically depicted in FIG. 2c. Preferably, however, the cavity 35 is closed. In this way there is no communication between the cavity 35 and the reactor 1, i.e. the liquid in the light distributor 30 is hermetically sealed from the environment. Note that by way of example, in FIG. 2c a variant is schematically depicted wherein at least part of the cavity wall 36 comprises a reflector 37. As mentioned above, when the top surface 38 is closed, the light distributor 30 is substantially closed by light receiving surface 31; when the light distributor 30 would be open, i.e. top surface 38 would comprise an opening the light receiving surface 31 may at least partially coincide with cavity wall(s) 36. The light distributor 30 in FIG. 2c is schematically depicted with an opening 39. When the light distributor 30 is open, such as in for instance schematically indicated in FIG. 2c, at least part of the cavity wall(s) 36 may have the function of light receiving surface.

The light distributors 30 have a height h1, and in case of conically shaped distributors 30 (conical or parabolic), a diameter d1. In case of pyramidal shapes (square pyramidal or tetrahedron), or other shapes, the light distributors 30 have a width w1 and a length l1. Preferably, h1 is in the range of about 5-100 cm, and d1, w1, l1 are independently in the range of about 1-20 cm. The ratio's h1/l1, h1/w1 and h1/d1 are independently preferably in the range of about 5-30. The surface 31 arranged to receive light preferably has an area (indicated with reference 131) of about 4-400 cm$^2$, preferably in the range of about 4-100 cm$^2$. The tapered surface 32 arranged to transmit light to the aqueous liquid comprising the photosynthetic culture preferably has an area 232 of about 10-4000 cm$^2$. Preferably, surface 32 is about 2-50, especially about 2-40 times, more preferably about 4-30, especially about 5-30 times larger than surface 31. Hence, in an embodiment the ratio of the surface area 232 of surface 32 to the surface area 131 of surface 31 is in the range of about 2-50, especially 2-40, such as about 4-30, like for instance especially 5-30. The person skilled in the art may tune the ranges and ratios of the dimensions depending upon for instance on latitude the photo bioreactor will be applied and optionally on the algae species. When the light distributor 30 is open, i.e. top surface 38 may comprise opening 39, the ratio of the surface area 232 of surface 32 to the surface area 131 of surface 31 may be in the range of about 1-50. When the ratio of l1/W1 is not substantially 1, elongated light distributors 30 may be obtained, which are elongated along an axis perpendicular to the longitudinal axis 100 (see FIGS. 5a-5c and 6a-6c).

Figure 2D:
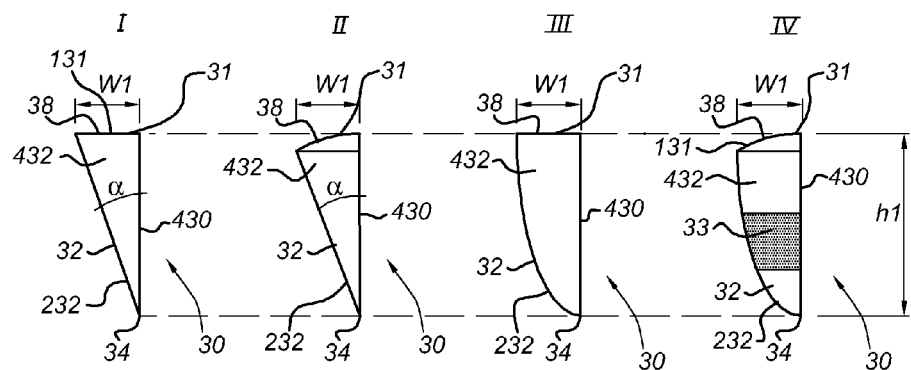
FIG. 2d schematically depicts a variation on these embodiments.

Referring to FIG. 2d, the light distributors 30 may also have asymmetrical shapes, for instance as schematically depicted in this figure. Part of the external surface that is arranged to be submerged in the aqueous liquid 21 during use of the photo bioreactor 1 may be substantially non-tapered straight and part of the external surface, may be tapered, i.e. may be tapered surface 32, as defined herein. Referring to types I and II, part of the external surface that is arranged to be submerged in the liquid 20 has α=0°, and part of the external surface that is arranged to be submerged in the liquid 20 has 0°<α<90°. This may be advantageous in relation to the latitude where the photo bioreactor 1 is to be applied. When using such asymmetric light distributors 30, in general about half of the external surface that is arranged to be submerged in the aqueous liquid 21 during use of the photo bioreactor 1 may be non-tapered straight (i.e. vertical relative to earth's surface or relative to the liquid surface 22), and half of the external surface that is arranged to be submerged in the aqueous liquid 21 during use of the photo bioreactor 1 may comprise the tapered surface 32 as defined herein. For the sake of understanding, the part of the external surface that is arranged to be submerged in the aqueous liquid 21 during use of the photo bioreactor 1 is further indicated with reference 432; the non-tapered (straight) surface is indicated with reference 430. Hence, the part of the external surface 430 that is arranged to be submerged does essentially not comprise light receiving surface 31. Hence, in an embodiment of the light distributor 30 according to the invention, the light distributor 30 has surface 31 arranged to receive light 40 and external surface 432 that is arranged to be submerged in the aqueous liquid 21 during use of the photo bioreactor 1, wherein at least part of the external surface 432 comprises tapered surface 32 arranged to emit at least part of the received light 40, and optionally part of the external surface 432 comprises non-tapered (straight) surface 430. As will be clear to the person skilled in the art, the ratio of the surface area of surface 432 to the surface area of surface 31 may be in the range of about 2-50, more especially about 5-30 (see further also above).

Also these embodiments may comprise a reflector 33, as indicated in FIG. 2d, type IV. Hence, in order to promote the number of reflections, in an embodiment at least part of the tapered surface 32 and at least part of the non-tapered surface 430 may comprises reflector 33 arranged to reflect at least part of the received light 40 back into the light distributor 30. In FIG. 2d1, such reflector 33 is shown. Preferably, the reflector occupies in the range of about 10-90% of the tapered surface 32 and the non-tapered surface 430; preferably, reflectors are only arranged in/on the upper part of the tapered surface 32 and non-tapered surface 430.

Further, as will be clear to the person skilled in the art, light distributors 30 with asymmetrically tapered surface 32 may also be applied. For instance, in an embodiment light distributor may have tapered surface 32 that is partly curved tapered and partly straight tapered. Assuming types I and III in FIG. 2d to be connected to each with mutual face 430, an embodiment of light distributor 30 with asymmetrically curved tapered surface 32 is obtained.

Figure 3:
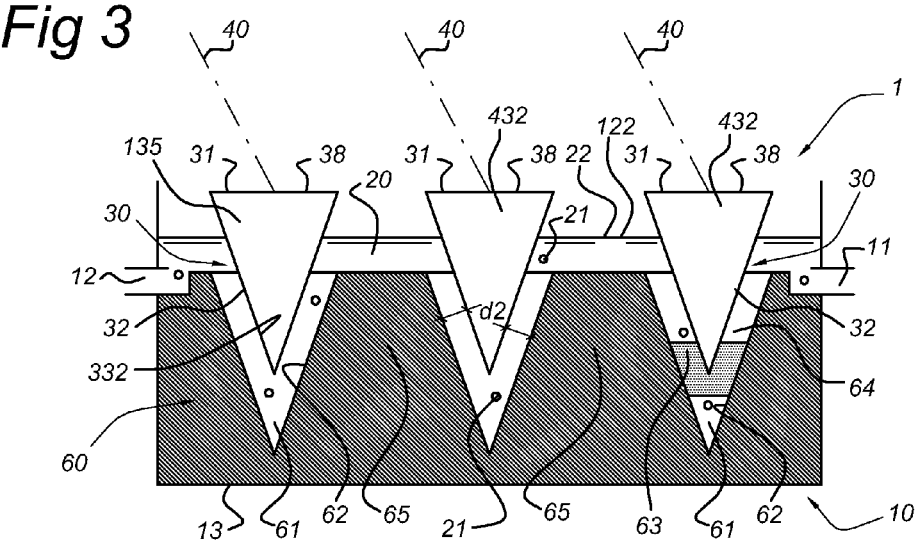
FIG. 3 schematically depicts in side view another embodiment of the photo bioreactor according to the invention.

In a specific embodiment, the photo bioreactor 1 according to the invention further comprises a second body 60. This is schematically shown in FIG. 3. This second body 60 comprises a cavity 61 having a tapered surface 62. In this way, in the vessel 10, such as a reactor or a (part of a) pond, the light distributor 30 and the second body 60 may be arranged in a configuration wherein the light distributor 30 is at least partly arranged in the cavity 61. To enable flow of the liquid 20, there is a distance d2 between the tapered surface 62 of the cavity 61 of the second body 60 and the tapered surface 32 of the light distributor 30. The light distributor 30 and the cavity 61 of second body 60 are in this way arranged in a male-female configuration. As will be clear to the person skilled in the art, the cavity 61 and the light distributor 30 preferably have substantially corresponding shapes. The shape of the tapered surface 62 of the cavity 61 substantially corresponds to the shape of the tapered surface 32 of the light distributor 30. For instance, when the light distributor 30 is a cone, a cone like cavity 61 is provided. Hence, the shape of the cavity 61, or its surface 62 on the one hand, and the shape of the light distributor 30, or its tapered surface 32 on the other hand are at least partially congruent and are constructed to allow the light distributor 30 enter at least part of the cavity 61 (male-female configuration), while maintaining at least distance d2 between the respective surfaces. The second body 60 may be arranged on the bottom of the vessel 10. For instance, such second body 60 may be arranged on the bottom of a pond, etc. In principle, the second body 60 may also be floating. The second body 60 may be made of one or more material(s) as described above, but may also consist of one or more other materials. In the embodiments described herein, it is not essential that the second body 60 comprises a transparent material.

The distance d2 between the light distributor 30 and the tapered surface 62 of the cavity 61 of the second body 60 may also be indicated as shortest distance. This distance may vary over the surface 62 of the cavity and the surface 32 of the light distributor 30. The distance d2 will in general be in the range of about 2-15 cm. Preferably, the distance is selected to have an optimum light distribution into the liquid 20. A larger distance d2 than the penetration depth of the light 42 is in principle not necessary. Due to the distance d2, a channel or void 64 is created between the light distributor 30 and the cavity 61. This channel may be used to enable a uniform flow. In this way, the light can substantially equally be distributed over photosynthetic culture 21, while flow in the cavity is such that it enables continuous refreshing of the culture on the surface and the middle of the channel.

Optionally, at least part of the tapered surface 62 of the cavity 61 of the second body 60 may comprises a reflector 63.

Preferably, the photo bioreactor 1 comprises a plurality of light distributors 30. The plurality of light distributors 30 may comprise for instance 10-10000 light distributors 30 per vessel 30. Further, the plurality of light distributors 30 may comprise more than one type of light distributors 30. The light distributors 30 of the plurality of light distributors 30 may have substantially the same dimensions but also a range of dimensions of the light distributors 30 may be applied. As mentioned above, the photo bioreactor 1 may comprise different types of light distributors 30 and during operation (during use) different types of light distributors 30 may be applied. Thus combinations of two or more different types of shapes of light distributors 30 may be applied in the photo bioreactor 1.

Correspondingly, preferably, the second body 60 comprises a plurality of cavities 61. The plurality of cavities 61 may comprise for instance 10-10000 cavities 61 per second body 60. Further, the plurality of cavities 61 may comprise more than one type of cavities 61 (i.e. differently shaped tapered cavities 61). The cavities 61 of the plurality of cavities 61 may have substantially the same dimensions but also a range of dimensions of the cavities 61 may be applied. The plurality of cavities 61 of the second body 60 create per se one or more protrusions 65 (i.e. the elevation(s) 65 between cavities 61). In fact, the combination of a plurality of light distributors 30 and the second body 60 comprising a plurality of elevations 65 can be seen as a plurality of stalactites and stalagmites wherein these are arranged offset from each other (i.e. a stalagmite is not right below a stalactite). The combination of a plurality of light distributors 30 and the second body 60 comprising the plurality of cavities 61 are preferably arranged in a male-female configuration, preferably such that each light distributor 30 is at least partially arranged in a cavity 61. Thereby, at least part of the tapered surface(s) 32 of the light distributor(s) 30 is circumferentially surrounded by at least part of the tapered surface(s) 62 of the cavity (cavities) 61. Hence, the invention is also directed to a method comprising providing a plurality of light distributors 30 and providing second body 60 comprising a plurality of cavities 61 and arranging the light distributors 30 and the cavities 61 in a male-female configuration (for instance in vessel 10).

Figure 4A:
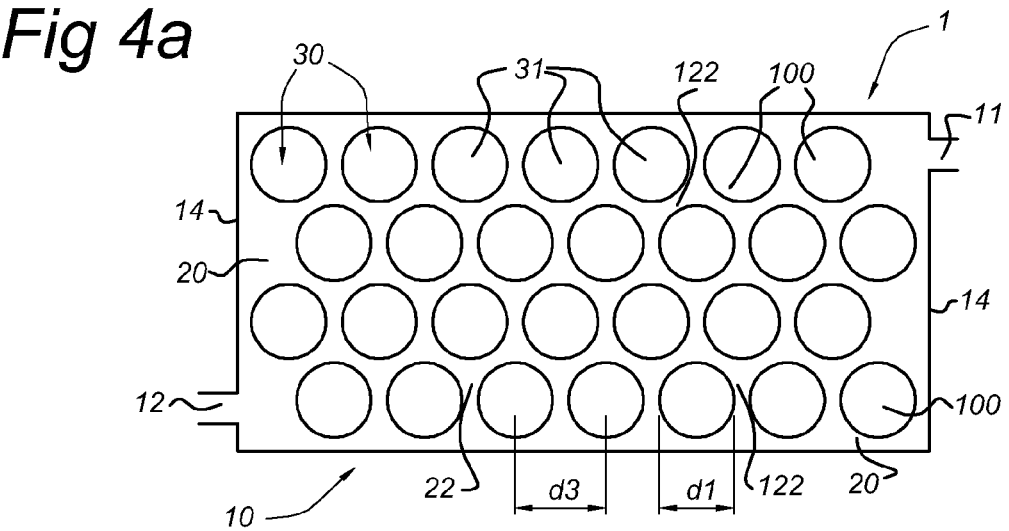
FIGS. 4a-4c schematically depict top views of embodiments of arrangements of light distributors in a vessel.
Figure 4B:
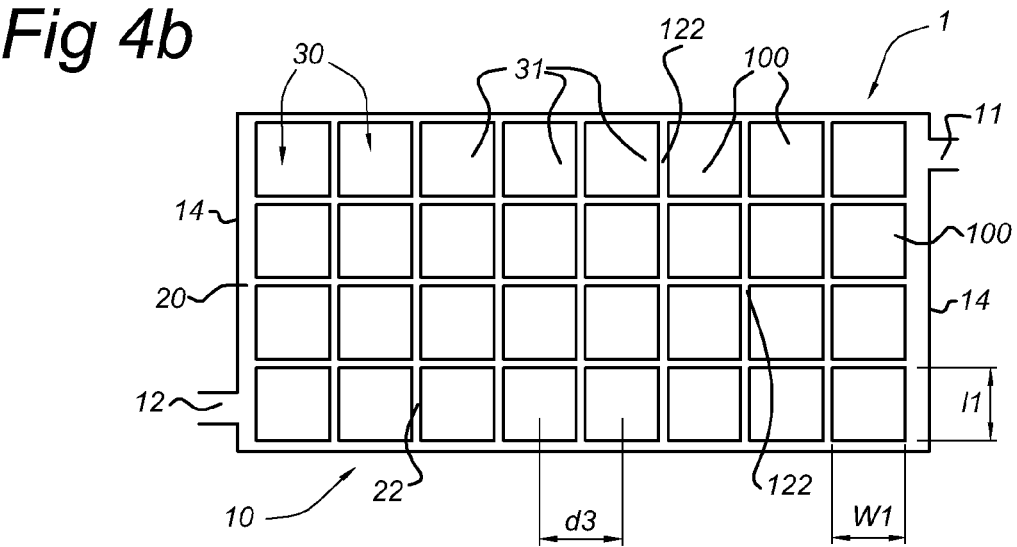
Figure 4C:
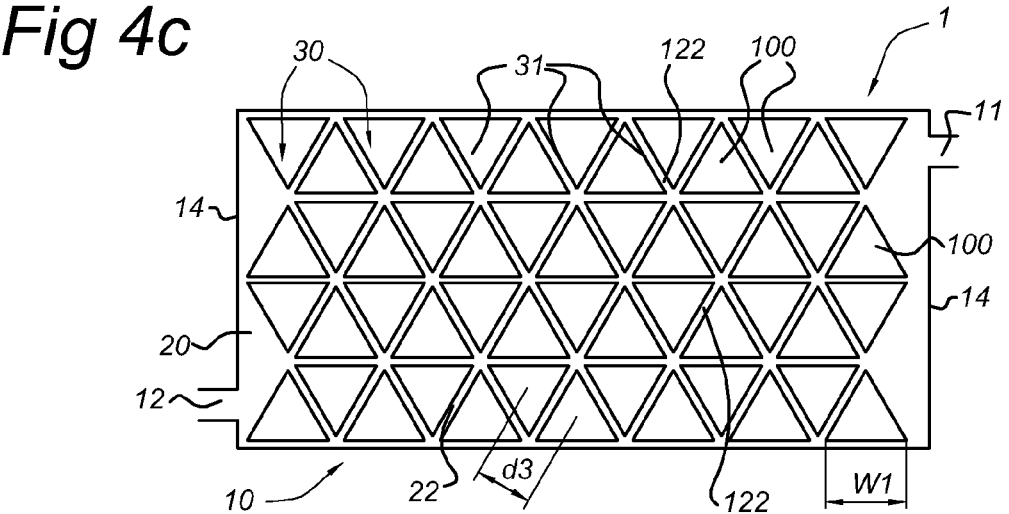

Embodiments of arrangements of a plurality of light distributors 30 are schematically depicted in top view in FIGS. 4a, 4b and 4c. FIG. 4a shows an arrangement of conically (including parabolic) shaped light distributors 30, FIG. 4b shows an arrangement of square pyramidal shaped light distributors 30 and FIG. 4c shows an arrangement of tetrahedral shaped light distributors 30. As will be clear to the person skilled in the art, combinations of differently shaped light distributors 30 may also be applied, for instance a plurality of conically and pyramidal shaped light distributors 30. These may preferably be regularly arranged (in the vessel 10). Preferably, the shape of the light distributor 30 and the corresponding cavity 61 are substantially the same; i.e. a conically shaped light distributor 30 and an inverse conically shaped cavity 61; a tetrahedral shaped light distributor 30 and an inverse tetrahedral shaped cavity 61, etc. Referring to FIGS. 4a, 4b and 4c, the light distributors 30 may be packed in a hexagonal packing, such as schematically depicted in FIGS. 4a and 4c, and in a cubic packing, such as schematically depicted in FIG. 4b. Preferably, a closed packing is applied, i.e. that the area of liquid surface 22 (under perpendicular irradiation) radiated directly by such radiation (this area is indicated in FIGS. 1, 3, 4a-4c and 6a with reference 122) and not radiated by light transmitted through the tapered surface 32 is as small as possible, while preferably the area of liquid 20 irradiated by light through the tapered surface 32 is as large as possible (this area is indicated in the side views in FIGS. 1, 3 and 6a with reference 332). Referring to FIGS. 1, 3, 6a and 6b, this may be the case when closed packings are applied, and where the light distributors 30 are adjacent to each other. Then, the light distributors 30 may be in physical contact to adjacent light distributors 30 (not depicted). Preferably, the light distributors 30 are arranged such that the longitudinal axes 100 are substantially parallel. Preferably, the light distributors 30 are in physical contact with adjacent light distributors 30.

The light distributors 30 may also have substantially spherical shapes (see also FIG. 14).

Figure 5A:
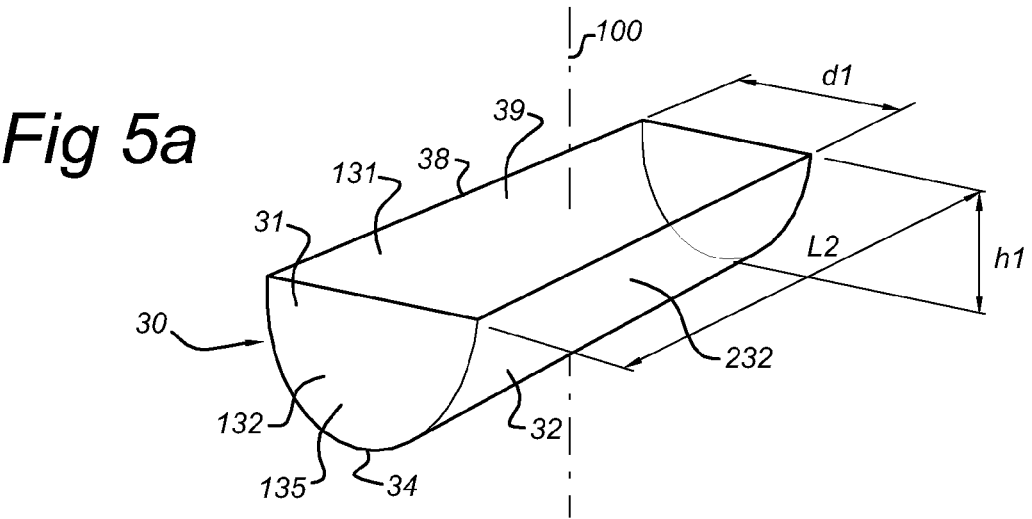
FIGS. 5a-5c schematically depict embodiments of elongated light distributors.
Figure 5B:
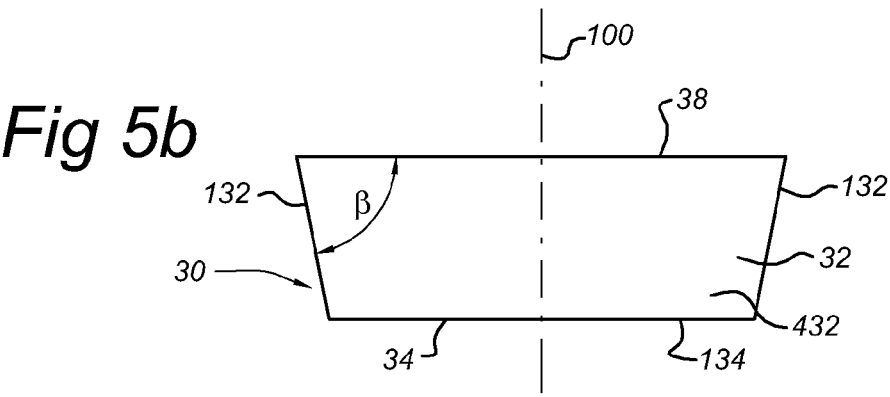
Figure 5C:
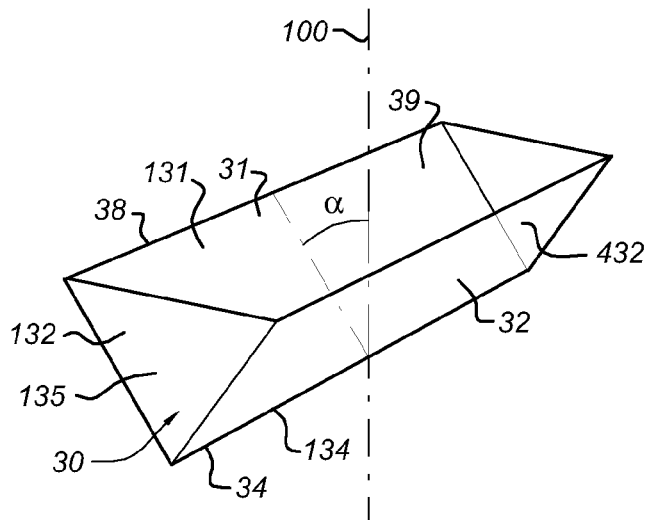

Further embodiments of the light distributor 30 are schematically depicted in FIGS. 5a-5c.

In FIG. 5a, the light distributor 30 has an elongated curved shape or an elongated parabolic shape. Referring to FIG. 2a, types III and IV, the light distributor 30 as schematically depicted in FIG. 5a could by way of illustration be obtained by an elongation along one axis perpendicular to longitudinal axis 100. In this way a kind of curved, or more especially parabolically, tapered surface 32 may be obtained. Especially a parabolic curved tapered surface 32 gives good results. Further, this embodiment is indicated as elongated curved light distributor 30. Such elongated curved light distributor 30 may be hollow or may be closed, i.e. top surface 38 may comprise an opening (as indicated in FIG. 5a with reference 39) or may be closed. Especially, such top surfaces 38 comprise opening 39. Surface 31 arranged to receive light is therefore the inner surface of the elongated curved light distributor 30.

The curved tapered surface 32 has an end part 34, and since this end part is also elongated, this end part may also be understood as taper edge, indicated with reference 134. Further, the elongated curved light distributor 30 may have a front and back surface, indicated with reference 132. Hence, in a specific embodiment, the elongated curved light distributor 30 is a partial enclosure, formed by tapered surface 32 and front and end surface 132.

The length of such elongated curved light distributor 30, indicated with reference L2, may for instance be in the range of about 0.5-10 m, such as about 1-5 m. The width d1 may for instance be about 1-50 cm, such as about 1-20 cm, especially about 10-20 cm. The height h1 may be about 5-100 cm, about 10-50 cm, especially 20-40 cm. The ratio's h1/l1, h1/w1 and h1/d1 are independently preferably in the range of about 5-30. The ratio of the length L2 and height h1, will at least about be 1, more especially at least about 5, even more especially at least 10. For instance, the ratio L2/h1 may be in the range of about 1-1000, such as about 2-200.

Preferably, surface 32 is about 2-50, especially about 2-40 times, more preferably about 4-30, such as preferably about 5-30 times larger than surface 31. Hence, in an embodiment the ratio of the surface area 232 of surface 32 to the surface area 131 of surface 31 is in the range of about 5-30. Note however, as mentioned above, the cavity may be closed, for instance by light receiving surface 31, but may in an embodiment also be open, as schematically depicted in FIG. 2c. When the light distributor 30 is open, i.e. top surface 38 may comprise opening 39, the ratio of the surface area 232 of surface 32 to the surface area 131 of surface 31 may be in the range of about 1-50.

The front and end surface 132 may independently have an angle β relative to top surface 38; β may for instance 90°, and will in general be in the range of about 70-90°.

In another embodiment, a wedge-shaped light distributor is provided, as schematically depicted in FIG. 5c. Here, the same details as described above, especially in relation to FIGS. 5a and 5b apply, with the exception that the curved surface 32, is an elongated V-shaped surface 32. Thus, referring to FIG. 2a, types I and II, the light distributor 30 as schematically depicted in FIG. 5c could by way of illustration be obtained by an elongation along one axis perpendicular to longitudinal axis 100. In this way a kind of V-shaped or wedge-shaped tapered surface 32 may be obtained. Hence, the elongated V-shaped light distributor 30 or the elongated wedge-shaped light distributor 30 as schematically depicted in FIG. 5c may also be an embodiment of the light distributor 30 of the invention.

During use, the elongated V-shaped light distributor 30 or the elongated wedge-shaped light distributor 30, or the elongated curved light distributor 30 are arranged with at least part of the tapered surface 32 submerged in the aqueous liquid 20 comprising the photosynthetic culture 21. The photo bioreactor 1 may comprise one or more of such elongated light distributors 30. When a plurality of such elongated tapered light distributors 30 is applied, a kind of corrugated construction, indicated with reference 300, may be applied.

In FIG. 6a, schematically an embodiment of the photo bioreactor 1 is depicted, which further comprises construction 300, wherein a construction 300 comprises the plurality of light distributors 30. The light distributors 30 may for instance be arranged in such construction 300 or be integrated in the construction 300. In a specific embodiment, the construction 300 comprising the plurality of light distributors 30 is a corrugated construction 300, and the light distributors 30 are corrugations (as depicted).

As described above, the light distributors 30 may for instance have tapered surfaces which are wedge-shaped (or V-shaped) or curved, i.e. the corrugations may are wedge-shaped (or V-shaped) or curved (as depicted), especially parabolically curved (or parabolically tapered). During use, the corrugations are arranged with at least part of the tapered surface 32 submerged in the aqueous liquid 20 comprising the photosynthetic culture 21.

FIG. 6b schematically depicts such construction 300. Such construction 300 may be one integral piece of material. Hence, in an embodiment, the construction 300 comprising a plurality of light distributors 30 is a single unit, especially a single piece of material. The photo bioreactor 1 may optionally comprise a plurality of such constructions 300, and may optionally comprise supports and or joists (not depicted) for supporting the construction 300. The light distributors are schematically depicted with curved tapered surface 32, however, the tapered surface 32 may also be wedge-shaped, as mentioned above (see also FIG. 5c). Preferably however, the tapered surface 32 is parabolically tapered.

FIG. 6c shows an embodiment of construction 300, also comprising a plurality of light distributors 30, but which are not elongate, at least not in a direction perpendicular to the longitudinal axis, as described above, and as schematically depicted in FIGS. 2a-2d and 3a-3d and 4a-4c.

FIG. 6a schematically depicts an embodiment wherein the photo bioreactor 1 further comprises construction comprising the plurality of light distributors 30. FIGS. 6a-6b schematically depict embodiments wherein the construction 300 comprising the plurality of light distributors 30 is a corrugated construction 300, and the light distributors 30 are corrugations, especially wherein the light distributors 30 have tapered surfaces (32) which are wedge-shaped (see FIG. 5c) or curved (see FIGS. 6a-6c, and also FIGS. 5a-5b). Note that in FIGS. 6a-6c the light distributors 30 are not adjacent; they may however be adjacent.

An advantage of using the construction 300 may also be that relatively easy a closed photo bioreactor 1 may be provided. The term closed photo bioreactor especially relates to bioreactors that are substantially closed. This may not imply a hermetically sealed photo bioreactor 1, but a substantially closed photo bioreactor 1. The fact that in an embodiment the photo bioreactor is substantially closed but not hermetically sealed" is meant in the sense that the area 122 of liquid surface 22 radiated directly and not radiated by light transmitted through the tapered surface 32 is as small as possible (but not always zero), while preferably the area 332 of liquid 20 irradiated by light through the tapered surface 32 is as large as possible. Hence, the construction 300 may be used as a kind of cover to the photo bioreactor 1.

Especially, the shape and the dimensions of the light distributors 30 mentioned herein may be designed by the person skilled in the art to trap the light as much possible and to distribute this evenly over the liquid 20. The person skilled in the art may take due care of the latitude of the application of the photo bioreactor 1. As mentioned above, combinations of two or more different types of shapes of light distributors 30 may be applied in the photo bioreactor 1 or in the construction 300, such as wedge-shaped, parabolic, and asymmetric (see also below) light distributors 30, respectively.

Referring to FIGS. 5a-5c, 6a and 6b, also the corrugation(s) may be asymmetric, similarly as describe above. Likewise (as described above), this may apply to the light distributors 30 of construction 300 as schematically depicted in FIG. 6c. Hence, also the elongated light distributors 30, for instance in construction 300, may be asymmetric.

The photo bioreactor 1 may comprise an inlet for a carbonaceous nutrition for the photosynthetic culture, such as an inlet for $CO_2$; the liquid 20 may for instance be aerated, but air may also be bubbled through the liquid 20. Likewise, a $CO_2$ containing gas or pure $CO_2$ gas may be used to aerate or bubble the liquid 20. Hence, the photo bioreactor 1 may comprise an inlet for a $CO_2$ comprising fluid. Further, if desired, an aqueous liquid 20 comprising or not comprising the photosynthetic culture 21 may be added and/or removed. Hence, the photo bioreactor 1 (i.e. especially vessel 10) may further comprise an inlet for introducing the aqueous liquid 20 and optionally an outlet for removing the aqueous liquid 20. Especially, the photo bioreactor 1 may comprise an inlet and an outlet for introducing and removing at least part of the photosynthetic culture 21, respectively. As will be clear to the person skilled in the art, the photo synthetic culture 21 is preferably introduced and/or removed while being present in the liquid 20. Hence, the photo bioreactor 1 further comprises an outlet for removing at least part of the photosynthetic culture 21. Further, the photo bioreactor 1 may further comprise an inlet for introducing nutrition for the photosynthetic culture, such as minerals (in addition to $CO_2$). As will be clear to the person skilled in the art, one or more inlets and outlets may be combined. Harvesting of the photosynthetic culture 21 can be done by means known in the art. Preferably, there is a flow through the reactor. Hence, to this end the reactor comprises an inlet 11 and an outlet 12. Inlet 11 is arranged introduce aqueous liquid, optionally comprising the photosynthetic culture 21, and outlet 12 is arranged to remove aqueous liquid, and optionally photosynthetic culture 21. Hence, in an embodiment, harvesting the photosynthetic culture may be done by removing aqueous liquid 20 comprising the photosynthetic culture 21 through opening 12. Therefore, in an embodiment the photo bioreactor comprises one or more inlets for introducing one or more selected from the group consisting of a $CO_2$ comprising fluid, an aqueous liquid (optionally comprising the photosynthetic culture 21), and nutrition for the photosynthetic culture 21 and one or more outlets for removing one or more selected from the group consisting of the photosynthetic culture 21 and aqueous liquid 20. The terms "inlet" and "outlet" may also refer to a plurality of inlets and outlets, respectively. Peripheral equipment, optionally or not, known to the person skilled in the art such as pumps, valves, filters, recirculation pipe(s), heating equipment, illumination devices, temperature sensors, flow sensors, sensors for sensing the concentration of one or more chemicals, etc. are not depicted in the schematic drawings.

According to another aspect of the invention, there is provided a method for the production of a photosynthetic culture 21. An aqueous liquid 20 and the photosynthetic culture 21 (i.e. including providing an aqueous liquid 20 comprising the photosynthetic culture 21) is provided to the vessel 10, which will contain the liquid 20 during operation of the photo bioreactor 1. Further, one or more light distributors 30 according to the invention (vide supra) are provided to the photo bioreactor 1, i.e. are arranged in the vessel 10.

In an embodiment, in the presence of the liquid 20, the one or more light distributors 30 are arranged to submerge at least part of the tapered surface 32 of the light distributor 30 in the aqueous liquid 20. The one or more light distributors 30 may be arranged in the liquid 20 after providing the liquid 20, but when the one or more light distributors 30 are in an embodiment comprised in a construction, it is also possible that the photo bioreactor 1 is filled with liquid 20 and the photosynthetic culture 21 (i.e. including the embodiment of providing an aqueous liquid 20 comprising the photosynthetic culture 21) until at least part of the tapered surface(s) 32 of the one or more light distributors 30 are submerged in the liquid 20. As will be clear to the person skilled in the art, during use of the photo bioreactor 1, the liquid surface 22 will be maintained at a height such that the light receiving surface(s) 31 are at least partially below the liquid's surface 22 (see also above).

Light 40 is provided to the surface 31 arranged to receive light 40. Light 40 may be one or more of solar light or artificial lighting (such as Xe lamps and or Ne lamps). Preferably solar light is applied.

The method may further comprising providing one or more of a $CO_2$ comprising fluid, an aqueous liquid and nutrition for the photosynthetic culture; and harvesting at least part of the photosynthetic culture 21. Harvesting may be done by means known in the art. In order to have a good light distribution over the photosynthetic culture the method preferably further comprises providing a flow in the aqueous liquid 20 comprising the photosynthetic culture 21 (in the vessel 10). Such flow may be obtained by introducing aqueous liquid at for instance inlet 11 and removing aqueous liquid 20, and optionally the photosynthetic culture 21, via outlet 12. With this method, biomass can be produced, which can be used for generating energy and/or providing useful compounds such as fatty acids, etc.

In the above schematically depicted embodiments, the photo-bioreactor 1 comprises vessel 10. However, the photobioreactor 1 does not necessarily comprise such vessel 10. The liquid 20 may also substantially only be contained in channels 64 arranged between the light distributors 30 in construction 100 and cavities 61 of second body 60. FIGS. 7a-7f schematically depict a non-limiting number of embodiments of "corrugated double structure", i.e. wherein both the plurality of light distributors 30 have the form of corrugations, especially a construction 300 which is corrugated, herein further also indicated as corrugated construction 300, but wherein also the second body 60 with the cavities 61 has the from of a corrugated structure, herein indicated as corrugated counter construction 600. Preferably, the photo bioreactor 1 of the invention is a closed photo bioreactor. FIGS. 7a-7e are in front view; FIG. 7f is a perspective front/side view.

With reference to these figures, a photo bioreactor 1 is schematically depicted, which comprises the aqueous liquid 20 comprising the photosynthetic culture 21. A plurality of light distributors 30 is provides (here schematically 3), wherein the light distributors 30 have, as also described above, surfaces 31 arranged to receive light 40 and tapered surfaces 32 arranged to emit at least part of the received light 40. At least part of the tapered surfaces 32 is submerged in the aqueous liquid 20 comprising the photosynthetic culture 21. In other words, at least part of the tapered surfaces 32 is in contact with the aqueous liquid. The light distributors 30 are herein not independent structures, but are contained in a construction 300. In fact, here, the construction is shaped to provide the plurality of light distributors 30. Hence, the photo bioreactor 1 further comprises construction 300 comprising the plurality of the light distributors 30. Especially, as schematically depicted in FIGS. 7a-7f, the construction 300 comprising the plurality of light distributors 30 is thus the above mentioned corrugated construction 300, and the light distributors 30 are corrugations, indicated with references 308. The construction 300 can be seen as the upper part or upper corrugations of the photo bioreactor 1

As mentioned above, the photo bioreactor may further comprise second body 60, which comprises a plurality of cavities 61 having tapered surfaces 62. The light distributors 30 and the second body 60 are arranged in a configuration wherein the light distributors 30 are at least partly arranged in the cavities 61. This provides distance d2 between the tapered surfaces 62 of the cavities 61 of the second body 60 and the tapered surfaces 32 of the light distributors 30, and thereby also form channels 64 between the tapered surfaces 32 and the tapered surfaces 62. Again, here, the cavities 61 (thus also protrusions 65) are not independent structures, but are contained in a construction, here indicated as corrugated counter construction 600. In fact, here, the construction 600 is shaped to provide the plurality of light cavities 61. Hence, the plurality of cavities 61 form the corrugated counter construction 600. Or, in other words, the second body 60 is arranged to form a corrugated counter construction 600. The light distributors 30 together, as construction 300, form corrugations 308; likewise, the cavities 61 (and protrusions 65) form corrugations, indicated with reference 608. The corrugated counter construction 600 comprise corrugations 608. The cavities 61 and the light distributors 30 preferably have substantially corresponding shapes. Or, alternatively this can be defined as that the corrugations 308 and corrugations 608 preferably have corresponding structures.

Figure 7A:
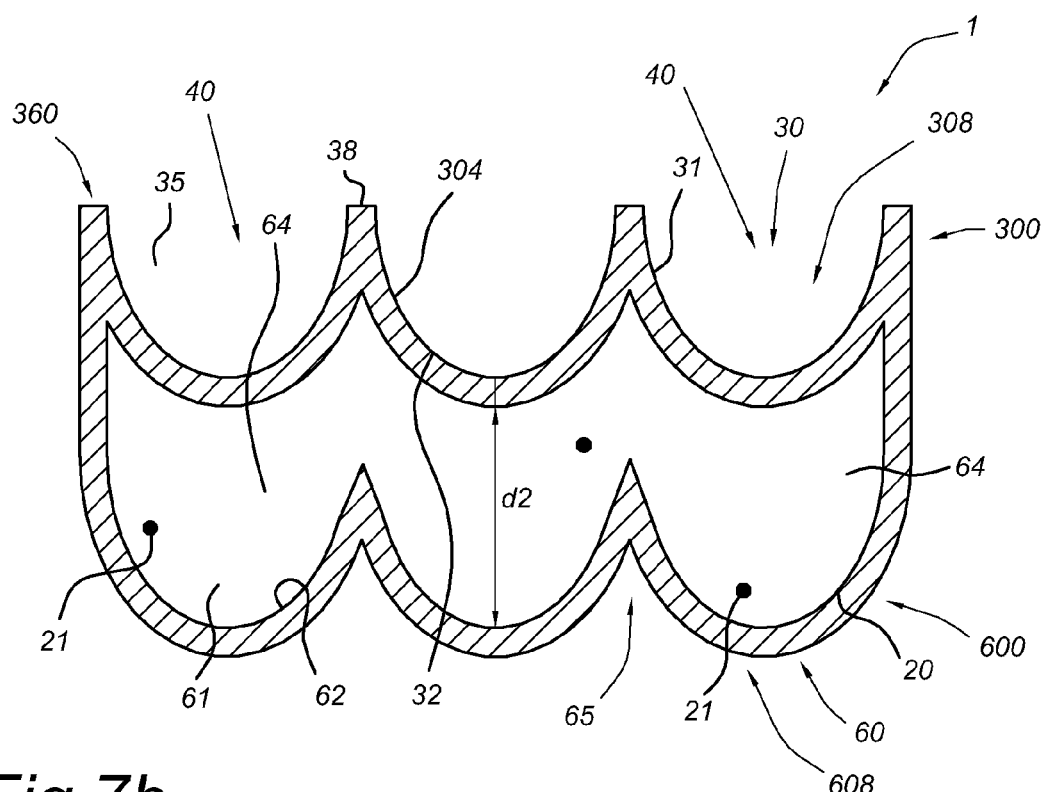
FIGS. 7a-7f schematically depict a number of embodiments according to the invention.
Figure 7B:
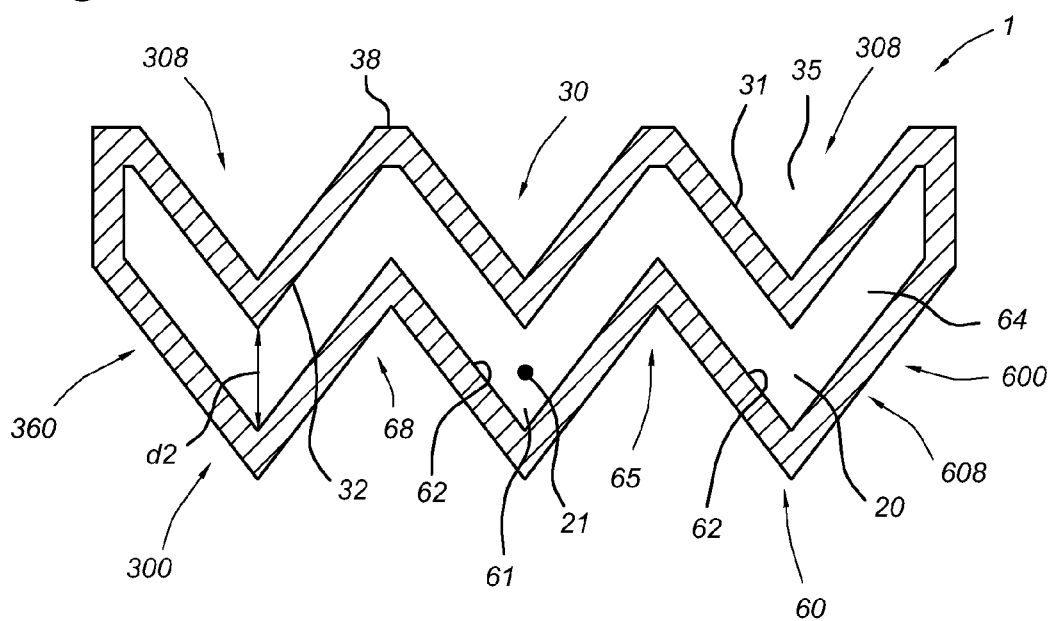

In FIG. 7*a* the shapes of corrugations 308 is parabolic and the shape of the corrugations 608 is also parabolic. In FIG. 7*b*, the shapes of corrugations 308 is edge-shape shaped (or V-shaped) and the shape of the corrugations 608 is also wedge-shape shaped (or V-shaped). Hence, in a specific embodiment, the corrugations 308 of the corrugated construction 300 and the corrugations 608 of the corrugated counter construction 600 have independently shapes which are selected from the group consisting of parabolic shapes, sine like shapes, wedge-shape shapes and block-wave shapes. Preferably, the shapes corresponding (and thus not independent). The light distributors 30 in both FIGS. 7*a* and 7*b* have an open top surface 38, and have cavities 35 (herein also indicated as light distributor cavities 35).

Especially, the construction 300 and the second body 60 are arranged to provide, preferably substantially parallel, channels 64 for containing the aqueous liquid 20, wherein the channels 64, thus preferably have substantially parabolic shapes, sine like shapes, wedge-shape shapes or block-wave shapes. Block-wave shapes are shapes similar to sheet-pile shapes. In this way, the photo bioreactor 1 may be arranged to create a flow of the aqueous liquid 20 comprising the photosynthetic culture 21 in a direction substantially parallel to the channels 64.

In a specific embodiment, the construction 300 and the second body 60, or more preferred, the corrugated construction 300 and the corrugated counter construction 600, are one reactor body, indicated with reference 360. Referring to FIGS. 7*a* and 7*b*, the photo-bioreactor 1 essentially consists of one reactor body 360, which substantially consists of construction 300 and second body 60, more especially, which substantially consists of corrugated construction and corrugated counter construction 600, which are arranged to provide (substantially parallel) channels 64 for the liquid 20. In this way, channel(s) 64 is (are) provided, which can also be defined as a kind of internal channel(s), i.e. internal in the reactor body 360. Light penetrates through the light distributors and gets into the liquid 20. An advantage of the one reactor body 360 is that the reactor may be relatively easily produced, processed, transported, connected to other reactor bodies and used. Such photo-bioreactors 1 comprising the reactor 360 may simply be arranged on surfaces like desert surfaces, (other) barren surfaces, beaches, on floating structures on water areas such as seas or lakes, etc.

The reactor body 360 may be made in different ways. For instance, construction 300 and counter construction 600 may be made independently and may be assembled into one construction i.e. the reactor body 360. In another advantageous embodiment, the construction 300 and the second body 60 are an extruded reactor body 360.

Therefore, in an embodiment, the invention also provides the reactor body 360 comprising the corrugated construction 300 and the corrugated counter construction 600, wherein the corrugated construction 300 and the corrugated counter construction 600 are arranged to provide (substantially parallel) channels 64 between the corrugated construction 300 and the corrugated counter construction 600 for containing the aqueous liquid 20 comprising the photosynthetic culture 21. As mentioned above, preferably, the corrugations 308 of the corrugated construction 300 and the corrugations 608 of the corrugated counter construction 600 (independently) have shapes which are selected from the group consisting of parabolic shapes, sine like shapes, wedge-shape shapes and block-wave shapes.

For the further discussion, only parabolic shaped corrugations 308 and 608 are depicted. However, the embodiments described and depicted below are not confined to such embodiments.

Figure 7C:
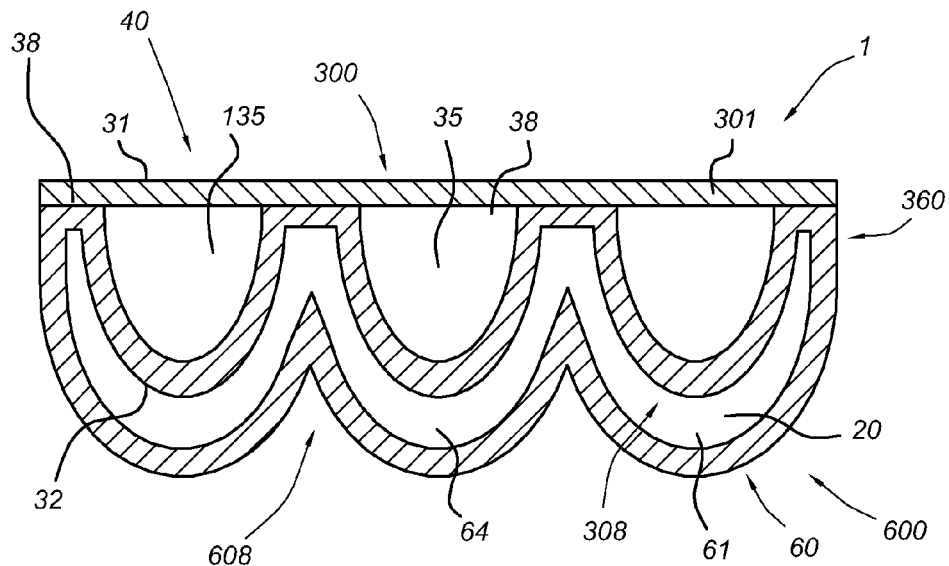
Figure 7D:
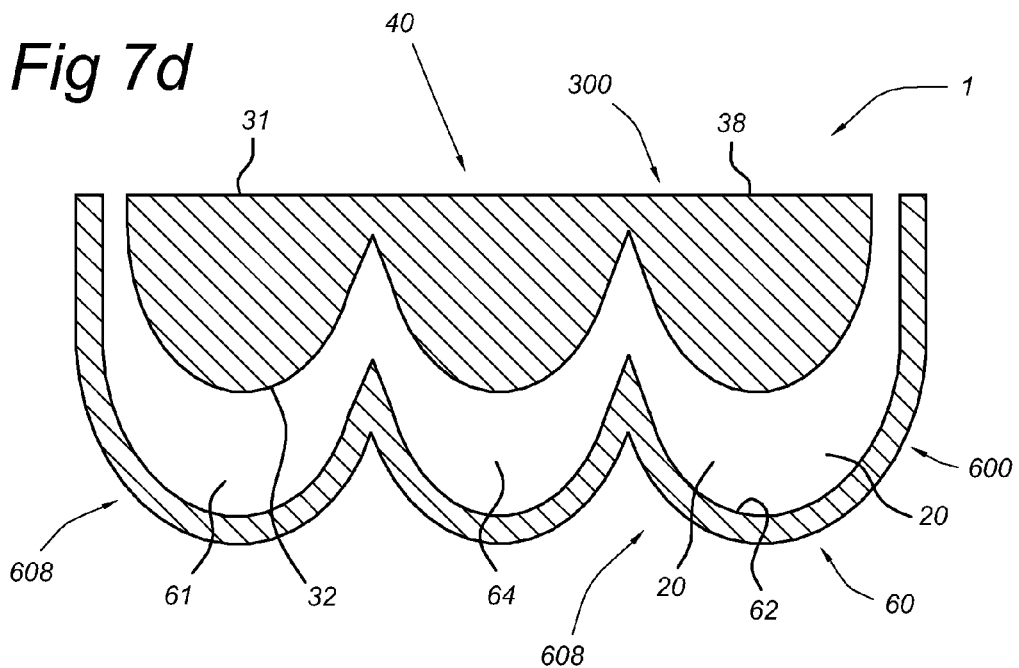

FIG. 7*c* schematically depicts an embodiment wherein the corrugations 308 are closed by a transparent cover 301. In this way, this transparent cover may comprise the surface(s) 31 arranged to receive light 40. Further, the cavities 35 are "covered" by this cover 301. FIG. 7*d* schematically depicts the corrugated structure 300 as massive body, with corrugations 308 and a substantially planar top face, which may again arranged to receive the light (and thus comprises the surface(s) 31 arranged to receive light 40). Here, the light distributors are massive bodies (without cavities 35).

Figure 7E:
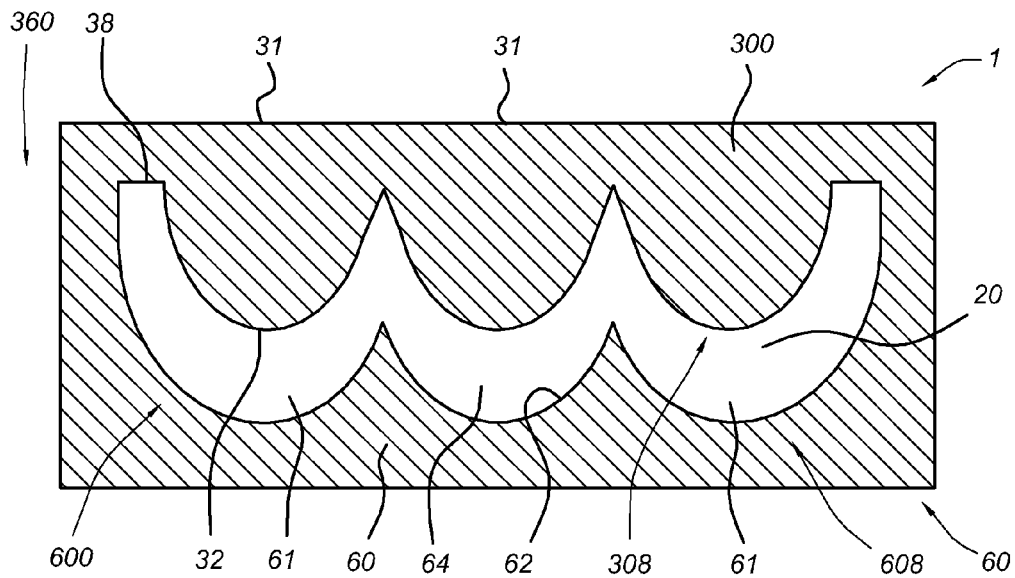
Figure 7F:
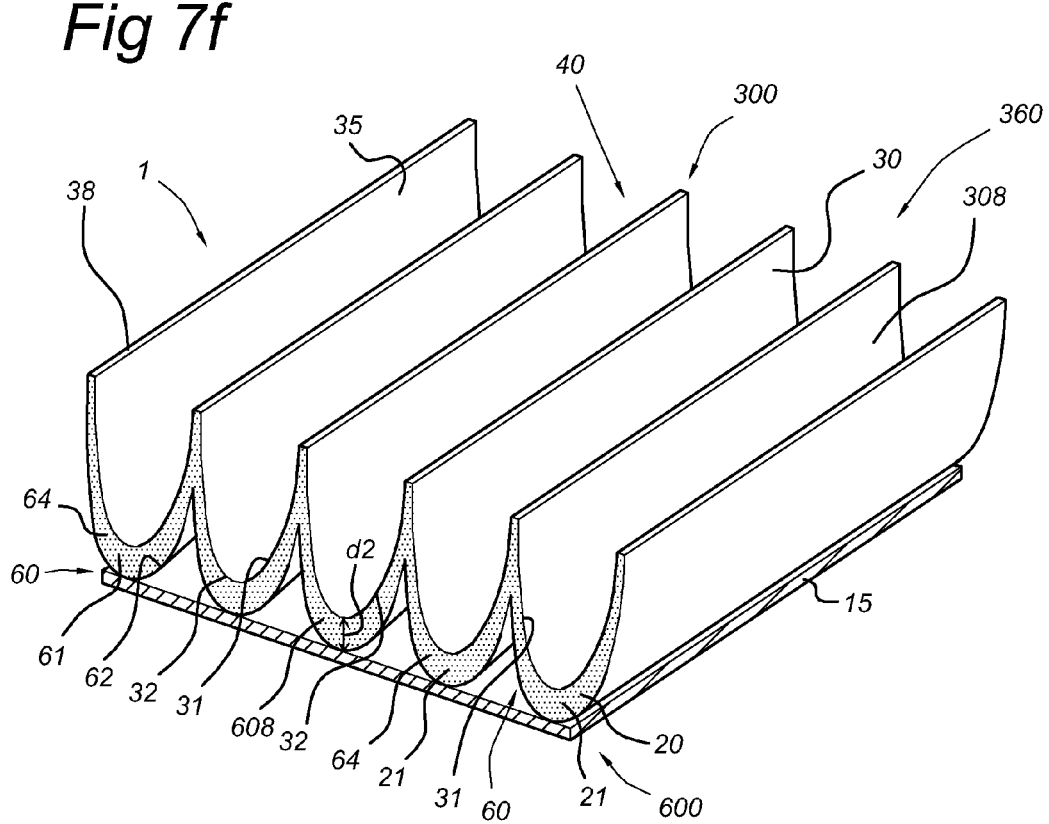

FIG. 7*e* schematically depicts an embodiment of the photo-bioreactor 1 comprising a single massive reactor body 360, with massive light distributors 30, wherein the corrugated construction 300 and corrugated counter construction 600 form one massive reactor body.

FIG. 7*f* schematically depicts substantially the same photo bioreactor 1 as depicted in FIG. 1*a*, but now in a perspective view. Further, the photo-bioreactor 1 is arranged on a support structure 15. This may allow arranging the photo-bioreactor 1, here with corrugations 608 as bottom.

Figure 8:
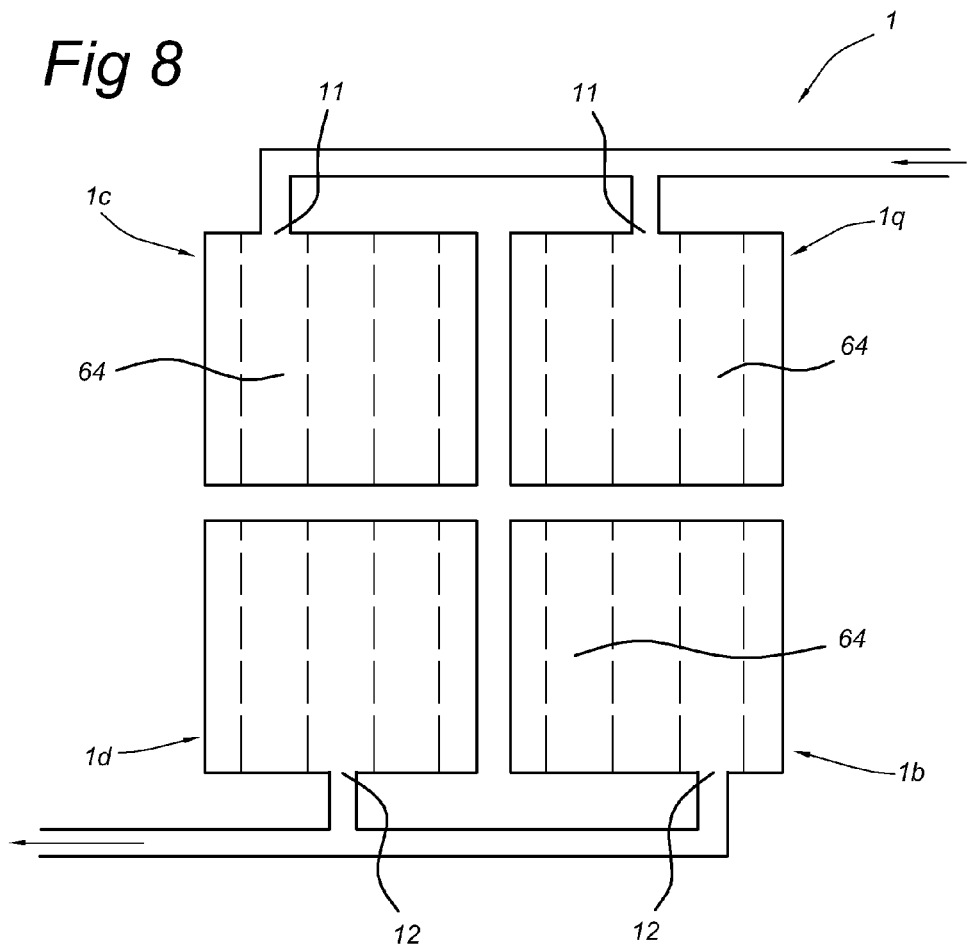
FIG. 8 schematically depict a reactor comprising a plurality of a series of connected reactors.

FIG. 8 schematically depicts (in top view) an embodiment of photo-bioreactor 1 comprising a plurality of photo-bioreactors 1, which embodiment is for the sake of understanding depicted with (only) 4 bioreactors 1, indicated with reference 1*a*-1*d*. Especially reactor bodies 360 may easily be arranged in series. Such photo-bioreactors 1 may be arranged in physical contact with each other, but also auxiliary tubes can be used to connect the channels 64 of adjacent (in series) arranged photo-bioreactors 1 to one another (here 1*a*-1*b* and 1*c*-1*d*, respectively).

The light distributors 30, and thus also corrugated construction 300, and optionally also corrugated counter construction 600, may have symmetric, but also may have asymmetric light distributors. In this way, an optimum light incoupling depending upon the intended latitude use of the photo bioreactor 1. Further, as mentioned above, preferably the corrugated construction 300, and optionally also corrugated counter construction 600 are preferably arranged in male-female construction at a distance (d) of each, thereby providing channel(s) 64.

The following figures show several embodiments of the light distributor, and its use in a photo-bioreactor, which can be produced in a cheap manner using a limited amount of raw materials. Furthermore, it can be produces in a mass production process such as vacuum forming, blow moulding and injection moulding, for example. To that end, the light distributors presented are thin-walled. They substantially keep their shape due to a filling liquid. The wall of the light distributors can in an embodiment be of elastomeric material and can another embodiment be a semi-rigid plastic material. It can be a film or foil, which may be elastic. The material thus allows the light distributor to obtain its shape much like a balloon, by its filling fluid 135. This filling liquid can be selected in such a way that the light distributors will be properly oriented with their light emitting surface below the aqueous liquid comprising said photosynthetic culture. The light distributors can have any of the features presented above. Several light distributors can be united to form a light distributor assembly.

Figure 9:
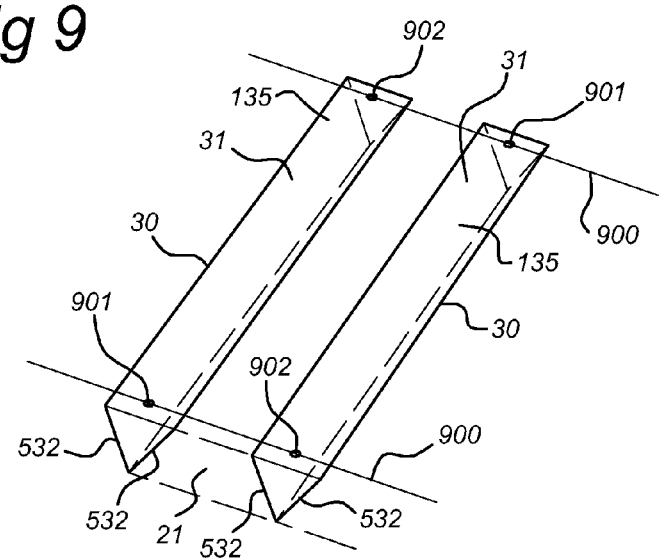
FIG. 9 shows an embodiment of elongated, wedge-shaped, interconnected light distributors.

In an embodiment shown in FIG. 9, a number of light distributors 30 is united to form a light distributor assembly. In FIG. 9, two light distributors 30 are shown. These light distributors 30 are here in the shape of elongated wedges.

They comprise walls of a thin, transparent or translucent material. The walls define a fluid filled cavity. In an embodiment, a light distributor 30 can comprise several cavities. The cavity or cavities can be fluid tight. The cavity or cavities can each have an inlet and an outlet for said fluid 135. This allow the fluid 135 to circulate. This can prevent the formation of bio film inside the light distributors which can reduce its effectiveness. Furthermore, it allows adjustment of the density and thus its position.

In an embodiment, these light distributor 30 can have walls made of a elastomeric material. In such an embodiment, the light distributor 30 can be filled with a fluid 135 having a pressure larger than the pressure of the aqueous liquid comprising the photosynthetic culture 21, or in such a way that the elastomeric material stretches more or less. This can define the shape of a light distributor 30, much like a balloon. In most of these embodiments, the fluid 135 is a transparent or translucent liquid, for instance based on water, or for instance glycerine. For safety reasons, often slightly salted water is used. Often, the salt level will be set to provide a slightly larger density then the aqueous liquid comprising the photosynthetic culture.

In an embodiment, the liquid has a density which can be comparable to the density of water. In an embodiment, the density of the fluid material is selected in such a way that the light receiving surface 31 extends above the surface of the aqueous liquid comprising the photosynthetic culture 21, and the light emitting surfaces 532 are largely below the surface of the aqueous liquid comprising the photosynthetic culture 21.

The walls defining the light receiving surface 31 and the light emitting surfaces 532 or the walls of the cavity or cavities of the light distributors can for instance be made of an elastomeric material as described above. In this embodiment, the elastomeric walls can be pre-shaped. In an alternative embodiment, the walls can be made from a plastic material. The material can be a plastic foil, for instance of PE, PP, PET like Mylar®, or the like. This foil can have a thickness of about 50 micron to about 2 mm. In these embodiments, the light distributors are kept in shape by means of the fluid 135 filling the light distributors. The foil can be pre-shaped using for instance a vacuum forming technique. In case these light distributors need to be larger in size, an even thicker material can be selected. In an embodiment, the foil is flexible and pre-shaped. The light distributor 30 may be kept in its shape by the fluid 135 filling the light distributor 30. In an embodiment, the fluid 135 is inserted at a pressure which stretches the foil, filling it like a balloon.

The light distributors 30 are coupled or connected to one another using a frame. In this embodiment of FIG. 9, the frame comprises lines 900 which are connected to the light distributors 30. The lines 900 can for instance coupled via rings connected to the light distributor. In another embodiment, the lines 900 can be or comprise tubes 900 which are couples to an inlet and outlet of a light distributor. In that way, inlets and outlets of different light distributors 30 are connected to one another. In that way, a fluid 135 material filling the light distributors 30 can flow though the light distributors. In this embodiment, the light distributors 30 have an inlet 901 and an outlet 902. In that way, for instance growth of algae or biofilm, which reduces the distribution of light, on the inside surface of the light distributors can be prevented. This is especially the case when the fluid 135 filling the light distributors 30 is water or is water-based, for instance salted water. The lines can in a be very simple embodiment be a rope, for instance from nylon, aramid, or other well known material. The line 900 can be fixed at the points 901, 902 in order to keep the light distributors positioned.

Figure 10:
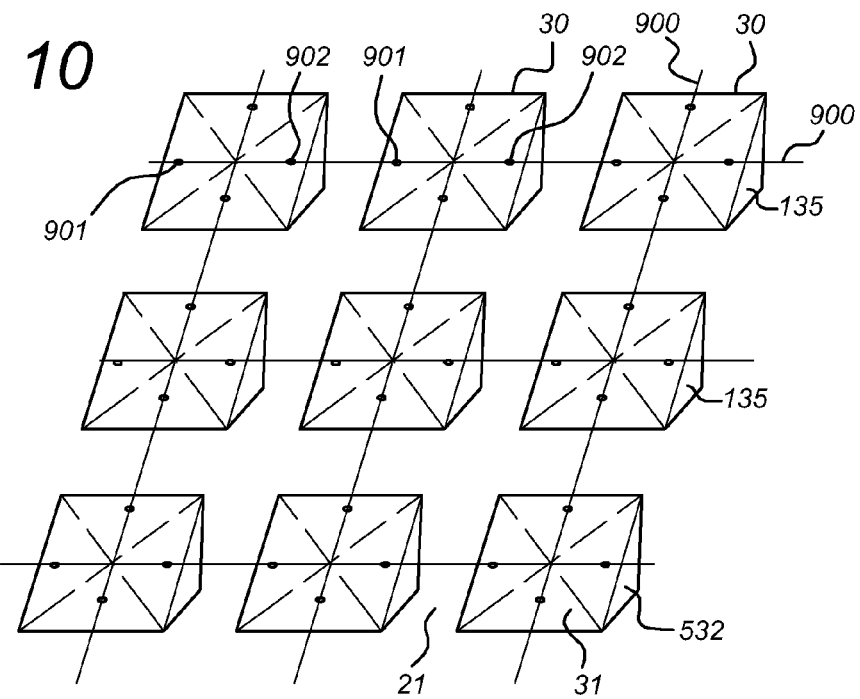
FIG. 10 depicts a series of pyramid shaped, interconnected light distributors.

FIG. 10 shows an embodiment of a light distributor assembly comprising pyramid-shaped light distributors 30. again, the light distributors are thin walled and fluid filled. It should be clear that the light distributors can have any shape for instance described in this description of embodiments. Again, these light distributors 30 are interconnected. In this embodiment the light distributors are interconnected via wires or tubes 900 which allow fluid 135 to flow from one light distributor to another. The connections are chosen in a way to kept the light distributors positioned in the aqueous liquid 21. It may also or next to this be possible to fill the light distributors 30 with a fluid 135 which make the light distributors 30 float in the aqueous liquid 21 with the light receiving surface 31 above the aqueous liquid 21 and the light emitting surfaces 532 below the aqueous liquid 21. Thus, it the density of the liquid can be a little below the density of the aqueous liquid, for instance about 5%-20% lower. Thus, a small part including the light receiving surface 31 will emerge above the aqueous surface.

Figure 11A:
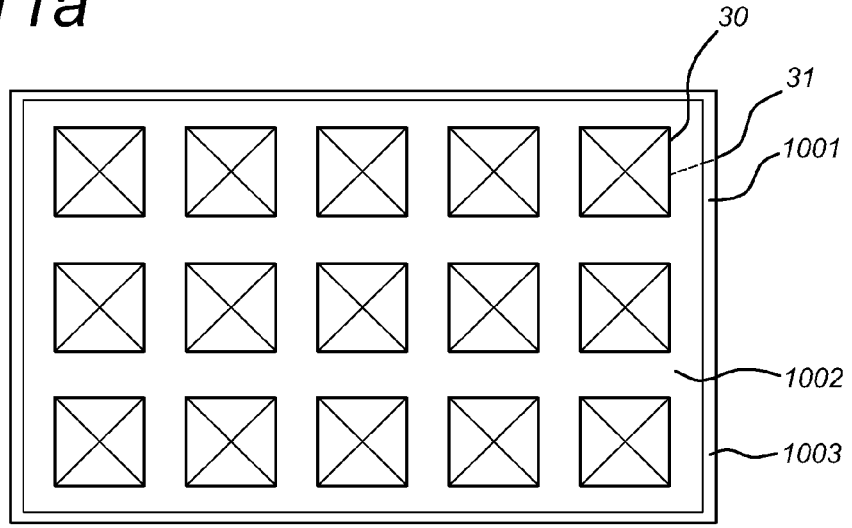
FIG. 11a shows a bottom view of a light distributor assembly made from thin sheets of plastic.

In the embodiment shown in FIG. 11a, a bottom view of a light distributor assembly is shown. In this embodiment, a first layer of flexible or elastic polymer material 1001 is provided. Furthermore, a second layer with holes 1002 is provided. In this embodiment, the holes are pyramid-shaped. Other shapes mentioned in this description are also possible. For instance, a very simple shape would be a spherical, semi-spherical or a halve sphere. Alternatively, the light distributor may be cylindrical, or even rectangular, In fact, in an embodiment the light emitting surface is an as large as possible multiple of the light receiving surface. In this way, the light distributor assembly is integrally formed with light distributors 30 interconnected via sheet material. In order to further save material, material between the light distributors 30 can be taken away.

Figure 11B:
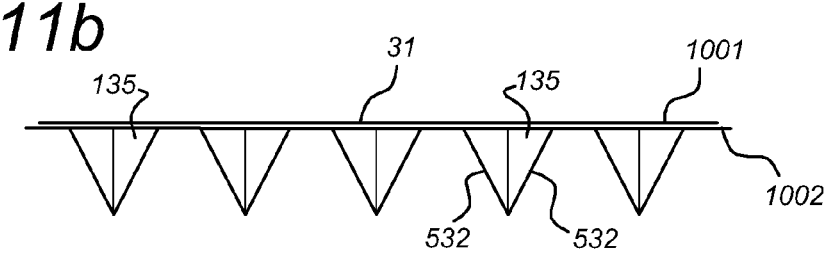

In FIG. 11b a cross section as indicated in FIG. 11a is depicted. Both the first layer 1001 and the second layer 1002 are clearly indicated. These layers can be made from thermoplastic material, making it easy to form and attach these layers.

Figure 12:
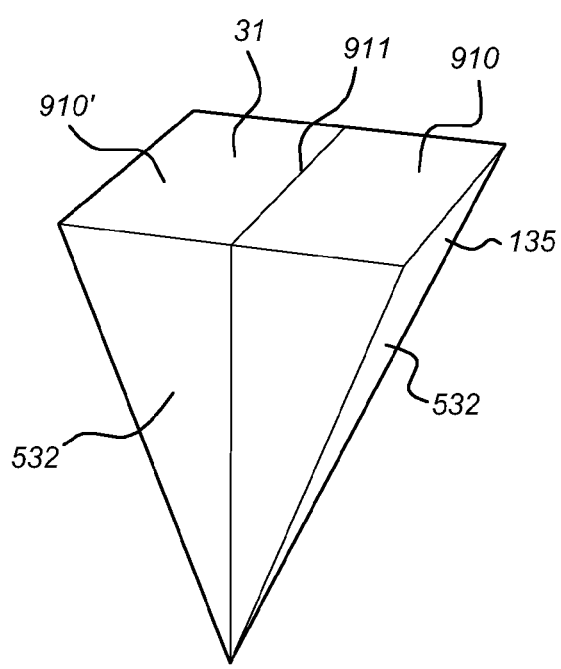
FIG. 12 shows a side view of a light distributor made from two parts.

FIG. 12 shows an embodiment of a light distributors 30 which is made from in this embodiment two parts 910, 910' which are attached in a fluid-tight manner. The two parts 910, 910' can be formed using moulding techniques, but also through deep-drawing techniques know in the field of packaging. The two parts are sealed together, for instance via heat at seam 911. They may also be glued together, for instance. Next, the light distributor is filled with a liquid already described above.

Figure 13:
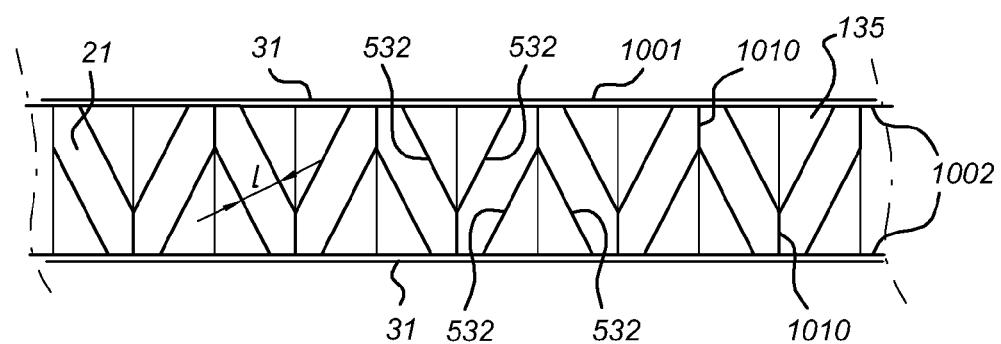
FIG. 13 shows a photo bioreactor having a light distributor assembly on one side and a light distributor assembly on the other side.

In FIG. 13 a photo bioreactor is depicted in cross section. In this embodiment, the light distributor assembly of FIGS. 11a and 11b can be used, for instance. It may however also be conceivable to use another, equivalent light distributor assembly. Two of the light distributors of these figures can be attached together in the way shown in this embodiment. It may also be possible to keep these light distributors positioned with respect to one another in another way in order to maintain an intermediate space between them and which can be filled with the aqueous liquid 21. The two parts are kept together and at a distance of about 1 via spacers 1010. These spacers 1010 can be ridged, or they can be cables. Aqueous liquids 21 can flow.

FIG. 14 shows several shapes of light distributor 30 comprises a partially in said aqueous liquid comprising the photosynthetic culture 21 submerged, fluid filled, light transmitting buoyant body. Said light distributors depicted in this drawing have shapes which vary from almost block-shaped, wedge-shaped, and spherical. These bodies are fluid-filled.

They have a thin, polymer film wall, for instance the already discussed Mylar® or equivalent material. They can be kept at their position via an alignment part. This alignment part can comprise a line 1010 attached in the bioreactor. Alternatively, it can be a part 1020 attached to the body or forming part of the body, for instance by being integrally moulded. This part 1020 may have a density larger than the density of the aqueous liquid 21. The bodies can be attached to one another in any of the manners described above in this description, for forming a light distributor assembly. In an embodiment, mylar® balloons filled with water or lightly salted water, i.e. with a salt contents a little higher than the salt contents of the aqueous liquid, may be used. It is even conceivable, as an alternative, to have fluid-filled balloons which rest on the bottom of a basin with aqueous liquid with the photosynthetic culture. These balloons then extend partly above the surface or the aqueous liquid to at least just below the surface of the aqueous liquid. They can extend to above this surface. In this way, they catch an optimal amount of light. These balloons are filled with a light transmitting fluid 135, preferably a transparent liquid. Thus, the received light is transported to deep inside the aqueous liquid. This fluid 135 may have the same density as the aqueous liquid, but the density may also be higher or lower, depending upon the desired configuration of the light distributors in the liquid. When resting on the bottom (such as the most right configuration in FIG. 14), their position is largely defined. This liquid may be water, or glycerine, or the like. These balloons can have a shape described in this description, for instance substantially spherical, cylindrical, block-shaped, pyramid shaped. As mentioned above, in a preferred embodiment, the light distributor(s) 30 comprise(s) (a) substantially spherical light distributor(s) 30 (see the two embodiments on the left in FIG. 14).

The invention is therefore also directed to the photosynthetic culture products obtained by the method for the production of the invention. Especially algae lipids are a mixture of storage lipids and membrane lipids. Eicosapentaenoic acid (one of the high value algae derived lipid product) is present in micro algae mostly in the form of glycolipids and phospholipids. When harvesting micro algae from the photo bioreactor 1 of the invention, the eicosapentaenoic acid (EPA) may be predominantly in the form of membrane lipid instead of storage lipid as the cells are presumably on the exponential growing phase. Since membrane lipids are much more abundant than the storage lipids, thereby the cultured cells may be more efficient in rendering the desired product. Micro algae (in particular Nannochloropsis) cultivated in the photo bioreactor may have about 40% or more by weight of lipids in the form of glyco-diacylglycerides and phospho-diacylglycerides, and at least about 5%, especially at least about 10% by weight of fatty acids consisting of EPA. In relation to other organisms that are growth under non-exponential growing conditions in the existing photo bioreactors, the organisms grown in the present photo bioreactor reach and maintain an exponential growing. Consequently the photosynthetic organisms (algae or others) that are produced with the present photo bioreactor present unique characteristics of high productivity yield and an elevated efficiency to synthesise the desired product.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The term "substantially" herein, will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

The photo bioreactor, light distributor and construction herein are amongst others described during operation. As will be clear to the person skilled in the art, the invention is not limited to methods of operation or devices in operation.

The invention claimed is:

1. A photo bioreactor (1), comprising:
  (a) an aqueous liquid (20) that comprises a photosynthetic culture (21) and
  (b) at least one light distributor (30) that comprises
    (i) at least one light receiving surface (31) arranged to receive light (40) and
    (ii) at least one emitting surface (532) arranged to emit at least part of the received light (40), wherein at least part of the emitting surface (532) is submerged in the aqueous liquid (20), and
  wherein said light distributor (30) comprises at least one fluid-filled sealed cavity that comprises walls of elastomeric material, and
  wherein said fluid (135) and elastomeric material in use transmit light from said light receiving surface (31) to said light emitting surface (532).

2. The photo bioreactor (1) of claim 1, wherein said fluid (135) has a pressure higher than the pressure of the environment, for maintaining the shape of said light distributor (30).

3. The photo bioreactor (1) of claim 1, comprising a plurality of said light distributors (30), coupled to one another via a frame.

4. The photo bioreactor (1) of claim 1, wherein said light distributor or distributors (30) comprise an inlet and an outlet for said fluid (135).

5. The photo bioreactor (1) of claim 4, comprising a plurality of said light distributors (30), coupled to one another via said inlets and said outlets, wherein said inlets are coupled to said outlets in fluid connection to allow the fluid (135) to flow through said light distributors (30).

6. The bioreactor (1) of claim 1, wherein the density of said fluid (135) is lower than the density of the aqueous liquid (20).

7. The bioreactor (1) of claim 6, wherein the density of the part of the light distributor (30) which extends furthest in the aqueous liquid (20) is greater than the density of the aqueous liquid (20).

8. The bioreactor (1) of claim 1, wherein the part of the light distributor (30) which extends furthest in the aqueous liquid (20) has an alignment part.

9. The bioreactor (1) of claim 1, wherein said light distributor (30) is formed from a plastic sheet having holes forming at least part of said emitting surface that extends into said aqueous liquid.

10. The bioreactor (1) of claim 9, wherein said holes are vacuum formed indentations in said plastic sheet.

11. The bioreactor (1) of claim 1, wherein said light distributor comprises a tip that extends into said aqueous liquid (20), wherein said tip has a density which orients said tip down in said aqueous liquid (20) when said light distributors float in said aqueous liquid (20).

12. The bioreactor (1) of claim 1, wherein said light distributor (30) is formed from a plastic sheet having holes forming at least part of said emitting surfaces extending into said aqueous liquid (20) and wherein said holes are indentations in said plastic sheet which is formed via blow molding or injection molding.

13. The bioreactor (1) of claim 1, wherein said light distributor (30) is substantially spherical.

14. The photo bioreactor according to claim 1, further comprising
(c) a construction (300) that comprises a plurality of said light distributors (30), in a corrugated construction (300), in which the light distributors (30) are corrugations (308).

15. The photo bioreactor (1) according to claim 1, further comprising
(c) a second body (60), comprising a plurality of cavities (61) having tapered surfaces (62), the light distributors (30) and the second body (60) being arranged in a configuration wherein
(i) the light distributors (30) are at least partly arranged in the cavities (61), and
(ii) the tapered surfaces (62) of the cavities (61) of the second body (60) are at a distance (d3) from the tapered surfaces (32) of the light distributors (30),
(iii) the plurality of cavities (61) form a corrugated counter construction (600).

16. The photo bioreactor (1) according to claim 1, wherein the shape of the light distributors (30) is parabolic or pyramid-like.

17. The photo bioreactor (1) according to claim 1, wherein the shape of the light distributors (30) is parabolic, sine-like or wedge-shaped.

18. The photo bioreactor (1) according to claim 15, wherein at least part of the tapered surface (32) comprises a reflector (33) arranged to reflect at least part of the received light (40) back into the light distributor (30).

19. The photo bioreactor (1) according to claim 1, wherein the plurality of light distributors (30) is 10-10000 light distributors (30) per vessel (10).

20. The photo bioreactor (1) according to claim 1, wherein the photo bioreactor (1) is a closed photo bioreactor (1).

21. The photo bioreactor (1) according to claim 1, wherein the light distributors (30) are hollow bodies with light distributor cavities (35) containing a liquid (135).

22. The bioreactor (1) of claim 1, wherein the light distributors (30) have substantially spherical shape.

23. A method for growing cells in a photosynthetic culture (21), comprising:
(a) providing an aqueous liquid (20) containing cells that constitute said photosynthetic culture (21) to a vessel (10) of the photo bioreactor (1) according to claim 1;
(b) submerging at least part of a tapered surface or surfaces (32) of the light distributor or distributors in the aqueous liquid (20) of the photosynthetic culture (20); and
(c) providing light (40) to the light distributor's surface or surfaces (31) that are arranged to receive light.

24. The method according to claim 23, further comprising generating a flow in the aqueous liquid (20) in the vessel (10).

25. The method according to claim 23, wherein the cells in the photosynthetic culture (21) comprise algae.

26. The method according to claim 23, wherein the cells in the photosynthetic culture (21) comprise microalgae.

27. The photo bioreactor according to claim 2, wherein said pressure is above atmospheric pressure.

28. The photo bioreactor according to claim 14, further comprising
(d) a second body (60), comprising a plurality of cavities (61) having tapered surfaces (62), the light distributors (30) and the second body (60) being arranged in a configuration wherein
(i) the light distributors (30) are at least partly arranged in the cavities (61), and
(ii) the tapered surfaces (62) of the cavities (61) of the second body (60) are at a distance (d3) from the tapered surfaces (32) of the light distributors (30), and
(iii) the plurality of cavities (61) form a corrugated counter construction (600).

29. The photo bioreactor according to claim 15, wherein at least part of the tapered surface (32) comprises a reflector (63) for the cavity.

30. The photo bioreactor (1) according to claim 28, wherein the construction (300) and the second body (60) are a single reactor body (360).

31. The photo bioreactor (1) according to claim 30, wherein the construction (300) and the second body (60) are an extruded reactor body (360).

32. The photo bioreactor (1) according to claim 28, wherein the construction (300) and the second body (60) are arranged to provide substantially parallel channels (64) for containing the aqueous liquid (20).

33. The photo bioreactor (1) according to claim 32, arranged to allow a flow of the aqueous liquid (20) in a direction substantially parallel to the channels (64).

* * * * *